(12) United States Patent
Friedman et al.

(10) Patent No.: US 11,026,654 B2
(45) Date of Patent: Jun. 8, 2021

(54) ELECTRONIC STETHOSCOPE WITH ACCESSORIES

(71) Applicant: Star Luminal LLC, San Antonio, TX (US)

(72) Inventors: David Julian Friedman, San Antonio, TX (US); Sarah Elizabeth Friedman, San Antonio, TX (US); Christopher Adam Leedy, Tucson, AZ (US); Ronald Graczyk, Cedar Park, TX (US)

(73) Assignee: Star Luminal LLC, San Antonio, TX (US)

( * ) Notice: Subject to any disclaimer, the term of this patent is extended or adjusted under 35 U.S.C. 154(b) by 0 days.

(21) Appl. No.: 16/723,119

(22) Filed: Dec. 20, 2019

(65) Prior Publication Data

US 2020/0205770 A1 Jul. 2, 2020

Related U.S. Application Data

(60) Provisional application No. 62/786,816, filed on Dec. 31, 2018.

(51) Int. Cl.
*A61B 7/04* (2006.01)
*H04R 1/46* (2006.01)
*H04R 1/10* (2006.01)

(52) U.S. Cl.
CPC ............ *A61B 7/04* (2013.01); *H04R 1/1025* (2013.01); *H04R 1/46* (2013.01)

(58) Field of Classification Search
CPC ........... A61B 7/04; H04R 1/46; H04R 1/1025
See application file for complete search history.

(56) References Cited

U.S. PATENT DOCUMENTS

| | | | |
|---|---|---|---|
| 4,783,813 A | 11/1988 | Kempa | |
| 4,878,501 A | 11/1989 | Shue | |
| 5,602,924 A | 2/1997 | Durand et al. | |
| 5,610,987 A | 3/1997 | Harley | |
| 5,844,995 A | 12/1998 | Williams | |
| 6,026,170 A | 2/2000 | Dieken et al. | |

(Continued)

OTHER PUBLICATIONS

ISA/US, International Search Report and Written Opinion issued in PCT/US19/68000, dated Feb. 27, 2020, 19 pgs.

*Primary Examiner* — Ping Lee
(74) *Attorney, Agent, or Firm* — Greenberg Traurig, LLP

(57) ABSTRACT

Electronic stethoscopes may have various accessories, modular components, and various configurations for powering the various components and accessories of the electronic stethoscope. In one embodiment, an electronic stethoscope apparatus includes a microphone configured to generate an electrical signal in response to received sound from a living subject; amplification circuitry; a speaker operably coupled to the amplification circuitry to output the electric signal after amplification; and a power supply configured to power the amplification circuitry. Circuitry for advanced signal processing may also be included, such as noise cancelling circuitry. The electronic stethoscope may also include removable electronic modules for wired or wireless headphones, battery packs, lights, and/or an electronic device for implementing the percussive method. An electronic stethoscope may also include components for implementing a laser enhanced stethoscope that can be used to pick up sounds from the surface of a living subject without making direct contact with the living subject.

20 Claims, 18 Drawing Sheets

(56) References Cited

U.S. PATENT DOCUMENTS

| | | |
|---|---|---|
| 6,932,186 B2 | 8/2005 | Costa et al. |
| 7,006,638 B1 | 2/2006 | Baekgaard et al. |
| 7,115,102 B2 | 10/2006 | Abbruscato |
| 7,533,758 B1 | 5/2009 | Frech et al. |
| 7,636,445 B2 | 12/2009 | Yoshimine |
| 7,991,165 B2 | 8/2011 | Kassal et al. |
| 8,200,277 B2 | 6/2012 | Lee |
| 8,827,920 B2 | 9/2014 | Lee et al. |
| 8,934,636 B2 | 1/2015 | Ferzli et al. |
| 8,934,637 B2 | 1/2015 | Habboushe et al. |
| 9,042,568 B2 | 5/2015 | Poplaw |
| 9,204,856 B2 | 12/2015 | Bedingham et al. |
| 9,265,478 B2 | 2/2016 | Wang et al. |
| 9,301,032 B1 | 3/2016 | Bello et al. |
| 9,414,803 B1 | 8/2016 | Naqvi |
| 9,756,419 B2 | 9/2017 | Renta |
| 9,770,224 B2 | 9/2017 | Park |
| 9,866,953 B2 | 1/2018 | Chong et al. |
| 9,931,099 B1 | 4/2018 | Fatteh et al. |
| 9,968,329 B2 | 5/2018 | Chong et al. |
| 2005/0154328 A1 | 7/2005 | Thierman |
| 2007/0154024 A1 | 7/2007 | Grasfield et al. |
| 2009/0060215 A1 | 3/2009 | Ocasio |
| 2009/0279708 A1 | 11/2009 | Habboushe |
| 2011/0096936 A1 | 4/2011 | Gass |
| 2011/0201968 A1 | 8/2011 | Goldstein |
| 2012/0190303 A1 | 7/2012 | Wong |
| 2016/0100817 A1 | 4/2016 | Hussain |
| 2016/0262717 A1 | 9/2016 | Smith |
| 2017/0027514 A1 | 2/2017 | Biederman et al. |
| 2017/0251997 A1 | 9/2017 | Chung et al. |

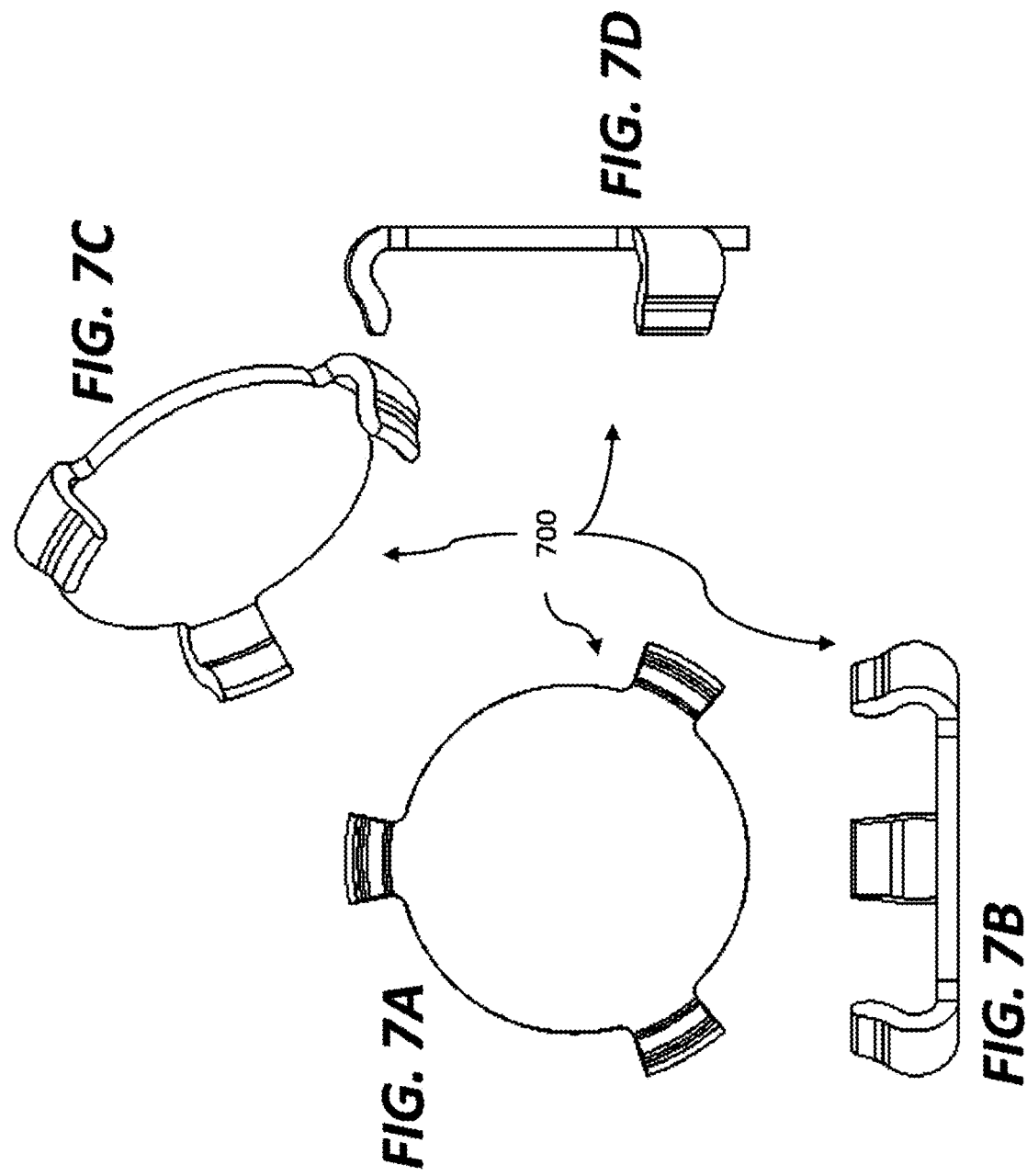

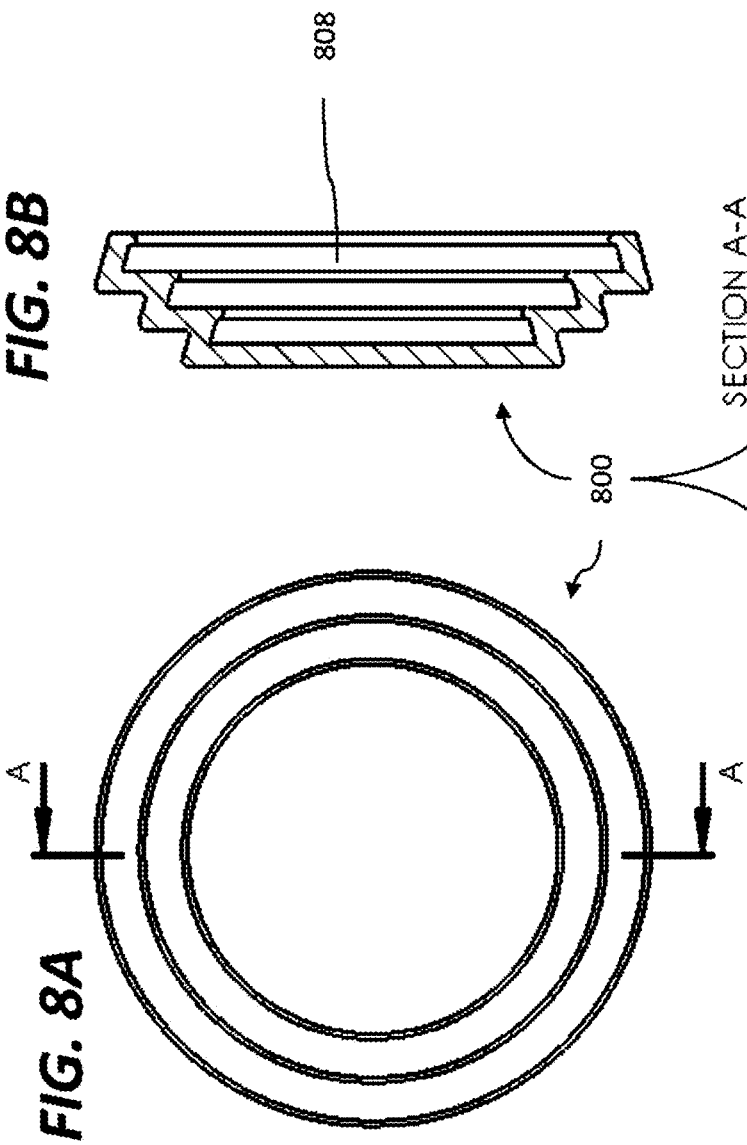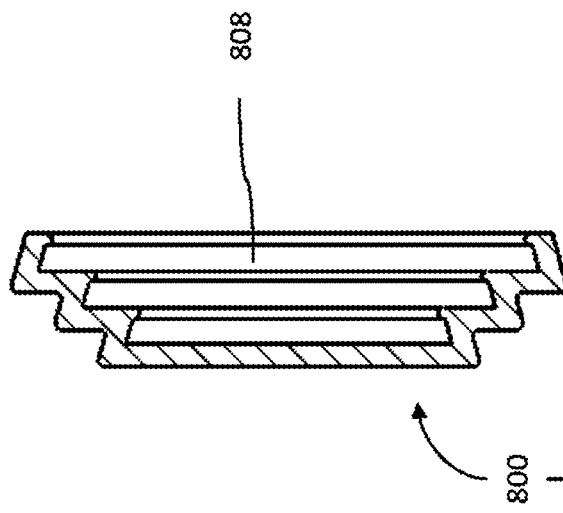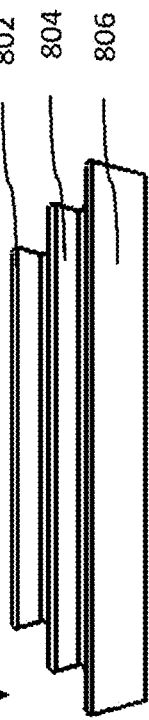

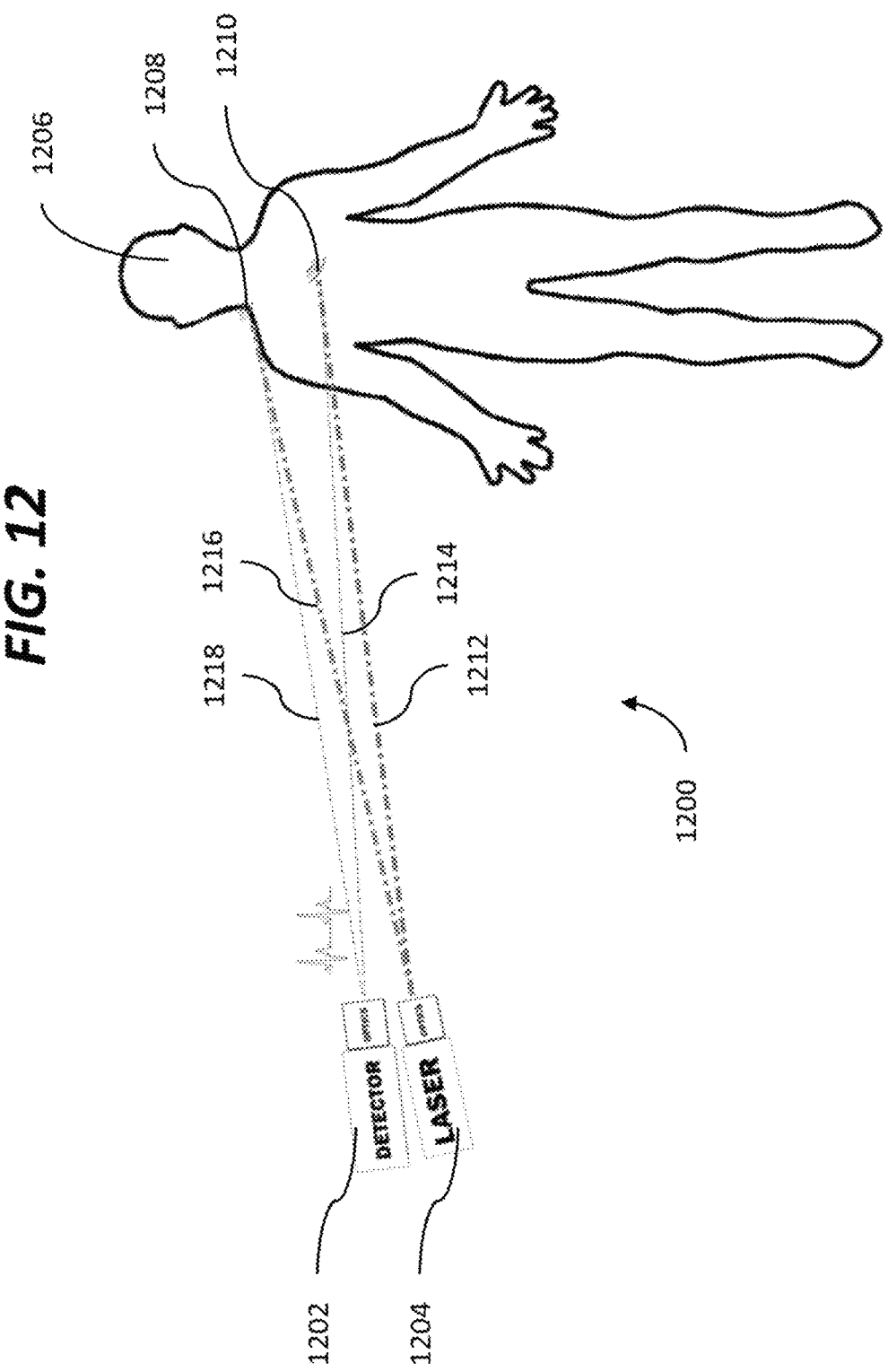

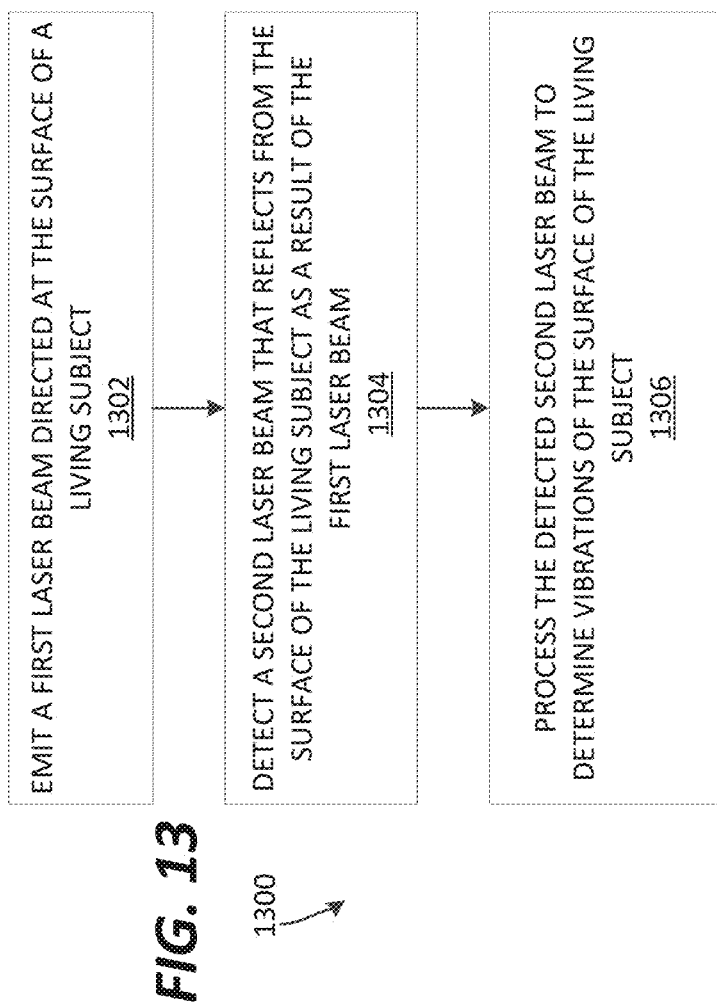

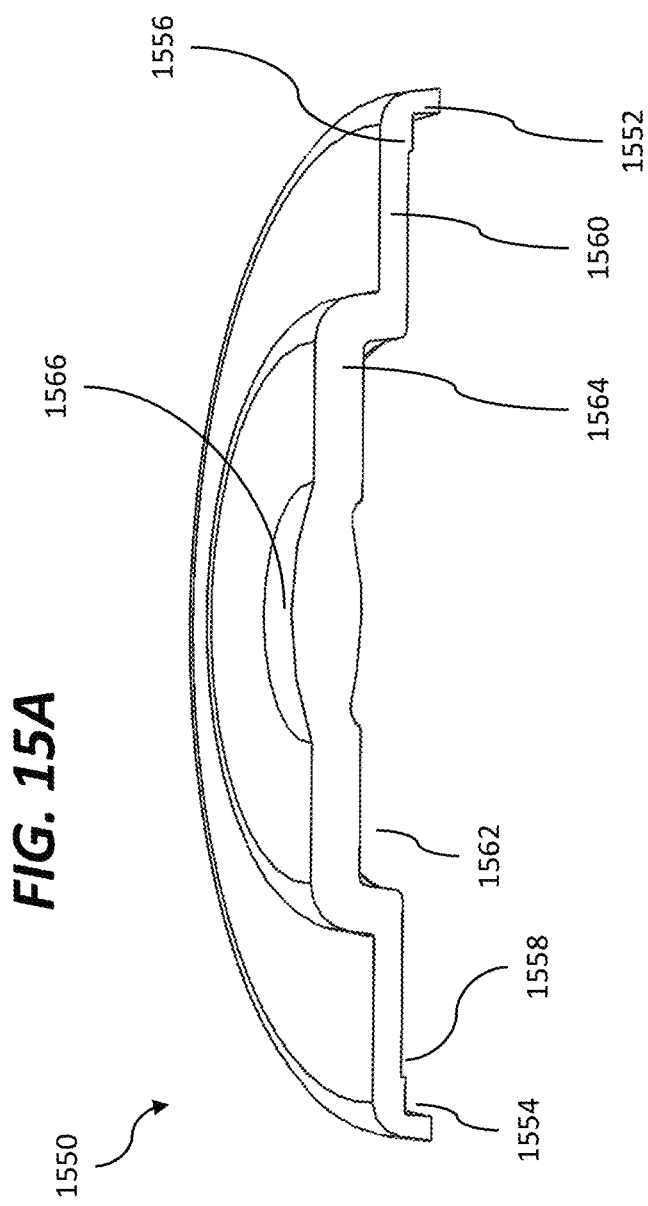

ELECTRONIC STETHOSCOPE WITH ACCESSORIES

CROSS-REFERENCE TO RELATED APPLICATION

This application claims the benefit of U.S. Provisional Patent Application No. 62/786,816, filed Dec. 31, 2018, the content of which is hereby incorporated by reference in its entirety.

BACKGROUND

The present disclosure relates to electronic stethoscopes and accessories for electronic stethoscopes.

A stethoscope is a medical device that may be used for auscultation, or the listening to of internal sounds of a living subject such as an animal or human body. Stethoscopes are often used by healthcare professionals to listen to lung, heart, artery, vein, intestine, and/or bowel sounds. Such use can help a healthcare professional identify clues for making a diagnosis of various illnesses or conditions. Stethoscopes are in such widespread use among healthcare professionals, that the stethoscope is often seen as a symbol of healthcare and/or healthcare professionals.

BRIEF SUMMARY

The following descriptions of examples of methods and systems are not intended to limit the scope of the description to the precise form or forms detailed herein. Instead, the following description is intended to be illustrative only and others may still follow and implement the teachings herein.

The instant disclosure provides for electronic stethoscopes with various accessories, modular components, and various configurations for powering the various components and accessories of the electronic stethoscope. For example, an electronic stethoscope may have electronic components that pick up sounds that can be processed, filtered, amplified, etc., to get a better or different sound than an acoustic stethoscope. In other examples, an electronic stethoscope as described herein may be an acoustic stethoscope that has additional electronic components, either for picking up sounds from a subject (e.g., for use as a stethoscope) or for other purposes (e.g., accessories to the stethoscope). For example, an accessory of a stethoscope may include a light that can be attached to or integral to the stethoscope for use in clinical diagnoses. In another example, accessories for listening to an electronically sensed sound may be part of a stethoscope, such as wired or wireless headphones. Another accessory may be a percussive device that causes a percussive force to impact the surface of a subject, which may be used in clinical diagnoses to determine density of an underlying structure. In other examples lasers may be used to accomplish, augment, or supplement the detection of vibrations on the surface of a subject without physical contact with that subject.

In one embodiment, an electronic stethoscope apparatus comprises: a microphone configured to generate an electrical signal in response to received sound from a living subject; amplification circuitry operably coupled to the microphone and configured to amplify the electric signal generated by the microphone; a speaker operably coupled to the amplification circuitry and configured to output the electric signal after amplification; and a power supply configured to power the amplification circuitry.

In one embodiment, a light apparatus comprises: a light; a switch to turn the light on or off; and a clipping mechanism configured to attach the light apparatus to a bell portion of a stethoscope, wherein the switch is accessible while the light apparatus is attached to the bell portion.

In one embodiment, an apparatus for applying a percussive force to a living subject comprises: a membrane having a first surface and a second surface, wherein the first surface is opposite the second surface; and a linear actuator configured to move a plunger linearly in response to application or removal of an electrical signal, wherein the linear actuator is configured to move the plunger such that the plunger impacts the first surface of the membrane and the membrane is configured to transmit a percussive force from the first surface to the second surface as a result of the plunger impacting the first surface of the membrane.

In one embodiment, a method is disclosed comprising: positioning an apparatus for applying a percussive force at a first location of a living subject; positioning an acoustic sensor at a second location of the living subject; applying a first electrical signal to a linear actuator causing a plunger to move linearly such that it impacts a first surface of a membrane, wherein the membrane comprises a second surface opposite the first surface and the membrane transmits a percussive force from the first surface to the second surface and into the living subject as a result of the plunger impacting the first surface of the membrane; and generating, by the acoustic sensor, a second electrical signal indicative of a response of the living subject to the plunger impacting the membrane and transmitting the percussive force into the living subject.

In one embodiment, an apparatus for measuring vibrations of a surface of a living subject comprises: an emitter configured to emit a laser beam directed at the surface of the living subject, wherein the laser beam is configured to interact with the surface of the living subject such that a reflected laser beam reflects from the surface of the living subject, and further wherein the reflected laser beam has different characteristics from the laser beam at least in part due to the interaction with the surface of the living subject; a detector configured to detect the reflected laser beam that is reflected from the surface of the living subject; and a processor configured to process the detected reflected laser beam to determine vibrations of the surface of the living subject.

In one embodiment, a method is disclosed for measuring vibrations of a surface of a living subject comprising: emitting a laser beam directed at the surface of the living subject, wherein the laser beam is configured to interact with the surface of the living subject such that a reflected laser beam reflects from the surface of the living subject, and further wherein the reflected laser beam has different characteristics from the laser beam at least in part due to the interaction with the surface of the living subject; detecting the reflected laser beam that is reflected from the surface of the living subject; and processing the detected reflected laser beam to determine vibrations of the surface of the living subject.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

FIGS. 7A-7D illustrate a clipping mechanism for an electronic accessory of a stethoscope according to some embodiments of the disclosure.

FIGS. 8A-8D illustrate a clipping mechanism for an electronic accessory configured to fit different sized stethoscopes according to some embodiments of the disclosure.

FIG. 12 is a schematic diagram of a laser detection device for measuring vibrations of a surface of a living subject according to some embodiments of the disclosure.

FIG. 13 is a flow diagram illustrating a method for measuring vibrations of a surface of a living subject according to some embodiments of the disclosure.

FIG. 15A illustrates a cross-sectional perspective view of a cover of the example light accessory of FIGS. 14A and 14B according to some embodiments of the disclosure.

DETAILED DESCRIPTION

Figure 1:
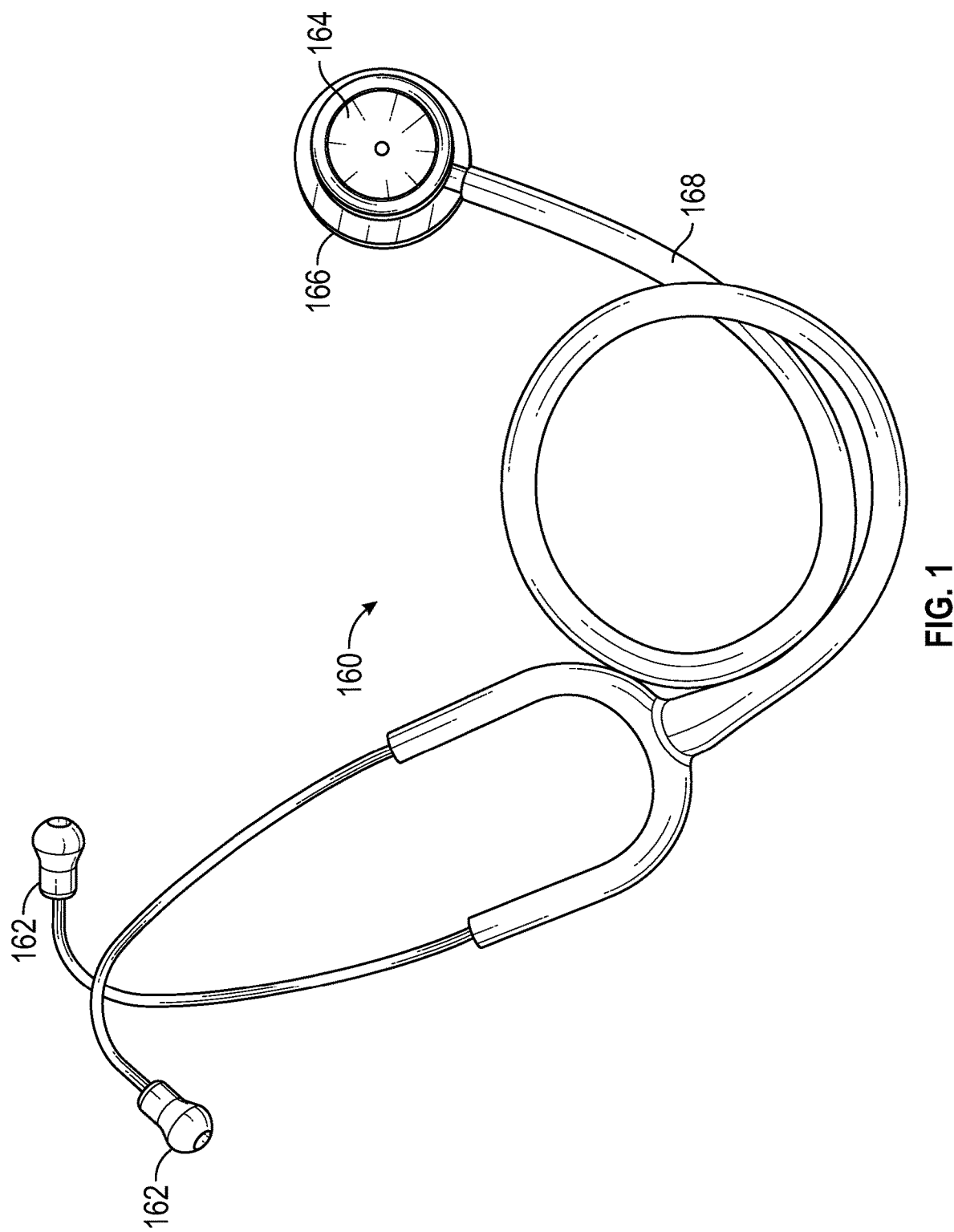
FIG. 1 illustrates a stethoscope according to some embodiments of the disclosure.

The present disclosure will now be described more fully hereinafter with reference to the accompanying drawings, which form a part hereof, and which show, by way of illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Described herein are electronic stethoscopes with various accessories, modular components, and various configurations for powering the various components and accessories of the electronic stethoscope. For example, an electronic stethoscope may have electronic components that pick up sounds that can be processed, filtered, amplified, etc. to get a better or different sound than an acoustic stethoscope. In other examples, an electronic stethoscope as described herein may be an acoustic stethoscope that has additional electronic components, either for picking up sounds from a subject (e.g., for use as a stethoscope) or for other purposes (e.g., accessories to the stethoscope). For example, an accessory of a stethoscope may include a light that can be attached to or integral to the stethoscope for use in clinical diagnoses. In another example, accessories for listening to an electronically sensed sound may be part of a stethoscope, such as wired or wireless headphones. Another accessory may be a percussive device that causes a percussive force to impact the surface of a subject, which may be used in clinical diagnoses to determine density of an underlying structure. In other examples lasers may be used instead of or in addition to stethoscopes for detecting vibrations on the surface of a subject without physical contact with that subject.

The various accessories and electronic stethoscope components may be used and implemented in different ways, including as modular components for either an electronic stethoscope or an acoustic stethoscope. The modularity of the various components described herein allow a user to add, subtract, replace, etc. various modules as described herein to improve the functionality of a stethoscope as desired by the user. In this way, a user may add a particular module to their stethoscope (whether electronic or acoustic) that gives the functionality they desire. This advantageously allows a user to only select modules they want, making those features more affordable than having to buy a stethoscope with components/features the user does not want or would not use. In other words, a user may tailor their stethoscope to their unique desires and needs using various modules described herein. In addition, modules may be replaced when they become worn or fail, modules may be upgraded when the user has more funds or desires additional functionality, and better modules may be developed over time and substituted by users over time to improve their electronic stethoscope without buying a completely new one. In various embodiments, multiple working modules of the same type may be used. For example, a first light module may be used while a second light module's battery is charging. In this way, modules may be swapped out for one another so that there is no downtime for the medical professional waiting, for example, for a module's battery to charge. A module may also be swapped out so that someone other than a doctor or healthcare provider may change out the battery instead of the doctor or healthcare provider. This allows the doctor or healthcare provider to focus on giving patient care rather than swapping out module batteries. In another example, modules may be sterilized or otherwise cleaned between uses. If multiple modules of the same type are used and available, a used/dirty module can be swapped out for a different, clean one so that there is no downtime. In other words, a first module may be used while a second module is cleaned, and after use of the first module it can be swapped out for the second module or still a third module that is already clean.

The various modular components described herein may also be used to enhance an electronic stethoscope or an acoustic stethoscope. For example, a light accessory, a battery pack, or other module as described herein may be used with either an electronic or acoustic stethoscope. Other modules may be used to enhance an acoustic stethoscope and turn it into an electronic stethoscope (e.g., install a module with a microphone, a module that includes a speaker or transmits to headphones, etc.). Some modules described herein may also be used with or without use of a stethoscope, such as the light accessory, the percussive device, and/or the laser enhanced listening methods described herein. Some modules may also be used in conjunction with one another, whether or not a stethoscope is also used. For example, a battery pack module may be used to power various modules/accessories whether or not a stethoscope is used. In another example, a battery pack may be used to power a light accessory, a percussive device, and or a laser enhanced listening method. In another example, a speaker or headphone module (e.g., as described below with respect to FIGS. 2 and 3) may be used with a percussive device and/or the laser enhanced listening methods, whether or not a stethoscope is used. Accordingly, various modules and accessories described herein may be used with and/or attached to a stethoscope (whether electronic or acoustic), may be used with one another, and/or may be used independently of a stethoscope. Such modularity and customization provides significant advantages for cost to the user, convenience and ease of use, portability, and many other advantages as described herein.

Various deficiencies of a standard acoustic stethoscope exist, which may be addressed by the various embodiments described herein. For example, ambient and background noise are a significant part of the auditory information picked up by an acoustic stethoscope. The tubes of a stethoscope may also be sources of ambient noise, which may corrupt a desired output. The physical form and materials of the acoustic stethoscope arbitrarily modify the information present at the skin surface which results in a lossy process for capturing sound data. Information may therefore be lost and the actual vibrations of the skin may be distorted.

FIG. 1 illustrates an acoustic stethoscope 160, which may be enhanced with various electronic components, accessories, etc. according to some embodiments of the disclosure. The stethoscope 160 includes a headset with ear pieces 162. The ear pieces 162 may be inserted into a healthcare professional's ears for performing auscultation of a living subject, such as a human or animal. A drum 166 includes a diaphragm (not visible in FIG. 1), which can be placed on the surface of the living subject. When the diaphragm is placed on the surface of the living subject, diaphragm is placed on the patient, sounds from the body vibrate the diaphragm, creating acoustic pressure waves which travel up tubing 168 to a listener's ears through the ear pieces 162.

A bell 164 opposite the drum 166 and diaphragm is concave in shape with a hole in the center, such that if the bell 164 is placed on the living subject, typically only the outer portion of the bell 164 would contact the living subject. In such an orientation, vibrations of the skin of the living subject directly produce acoustic pressure waves traveling up to the listener's ears through the tubing 168. The bell 164 typically transmits lower frequency sounds than the diaphragm of the drum 166. One side of a stethoscope may be used more often by certain healthcare professionals or for certain diagnostic purposes. Thus, certain accessories as described herein may be implemented according to such preferences or use patterns. As just one example, the diaphragm may be used by some healthcare professionals more often, so an accessory for a stethoscope such as a light may be configured to fit onto and/or into the bell 164 portion of the stethoscope. Additionally, the light may be removable from the bell 164 of the stethoscope 160 so that the bell 164 may still be used while the light is detached. In various embodiments, accessories may be attached to the stethoscope 160 so that no functional part of the stethoscope 160 (e.g., the diaphragm, the bell 164, the ear pieces 162) is blocked from use while the accessory is attached to or integrated in the stethoscope 160.

In various embodiments, the stethoscope 160 may also have other electronic components. For example, the stethoscope 160 may be modified to include electronic components, may include electronic components that are not visible in FIG. 1, and/or may be compatible with accessory electronic components that fit and/or are used with the stethoscope 160 as described herein.

Some electronic components may be configured as a module that is used to modify an existing stethoscope. For example, additional signal processing modules may be added to an electronic stethoscope. In another example, signal processing modules, speaker/headphone modules (e.g., as described below with respect to FIGS. 2 and 3), and/or microphone/detection modules may be implemented on an existing acoustic stethoscope to give it electronic stethoscope capabilities.

A microphone module may also be implemented in various ways in an existing acoustic stethoscope. For example, a microphone module may come with instructions for installing it into an existing acoustic stethoscope. The installation may occur in various ways. For example, a microphone module with instructions for how to embed an acoustic orifice that includes the microphone into the tubing of a stethoscope may be provided. Instructions may also include steps for cutting or otherwise modifying the tubing to install a microphone module. For example, a small hole or port may be put in the tubing according to included instructions or tubing may be cut so that a microphone module is spliced in line into the tubing. A module may also be a microphone that surface mounts onto the tubing of the stethoscope. A microphone module may also be inserted into the bell of the stethoscope. A microphone module may also be inserted between components of an existing stethoscope. For example, the tubing connected to the bell may be disconnected to insert a microphone module. After inserting the microphone module, the tubing and the bell may be reconnected, or the tubing and the bell may both connect to the microphone module such that the microphone module is now in between the bell and the tubing. Similarly, a microphone module may be inserted between other components, such as the tubing and the ear pieces of a stethoscope, or in any other location of the stethoscope.

Figure 2:
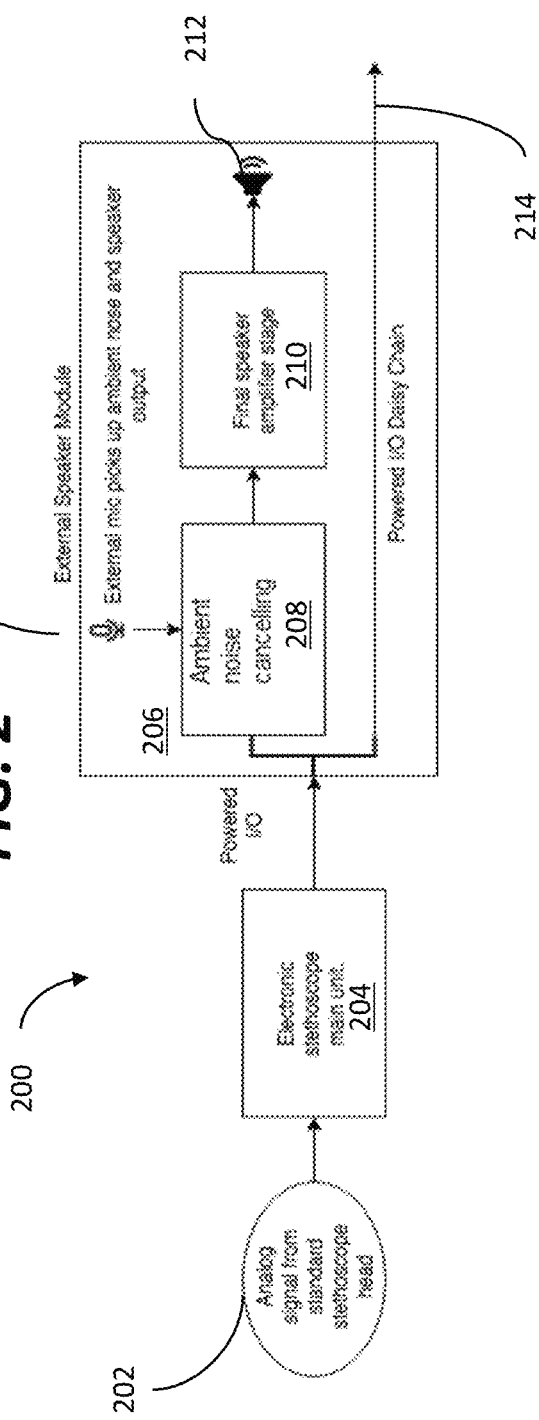
FIG. 2 is a schematic diagram of electronic stethoscope components with an external speaker module according to some embodiments of the disclosure.

FIG. 2 is a schematic diagram of electronic stethoscope components 200 with an external speaker module 206 according to some embodiments of the disclosure. For example, an electronic stethoscope may include a microphone that generates an electrical signal in response to received sound from a living subject. The sound generated may be an analog signal from a standard stethoscope head at 202, for example. The microphone may be included in circuitry of an electronic stethoscope main unit 204, for example.

As just one example, the microphone and any other circuitry of the electronic stethoscope main unit 204 may be embedded into tubing (e.g., the tubing 168 of FIG. 1) of a stethoscope connected between a diaphragm and an ear piece (e.g., one or both of the ear pieces 162 of FIG. 1). In this way, sound picked up by the diaphragm that passes into the tubing can also be detected by the microphone. In some embodiments, some or all components of the electronic stethoscope main unit 204 may be located in other parts of a stethoscope than the tubing, and some or all of the components may be removable from the stethoscope without affecting the functioning of the acoustic aspects of the stethoscope.

In various embodiments where components of the electronic stethoscope main unit 204 are installed in the tubing, the tubing allows acoustic sound waves to travel from the diaphragm to the ear piece even though the stethoscope also has a microphone and/or other electronic components. In this way, the microphone does not impede the acoustic sound waves from traveling within the tubing. In other words, the microphone may be spliced inline of the tubing so as not to impede normal acoustic use. Similarly, if components such as the microphone are located within a drum, bell, or other part of a stethoscope, those electronic components may similarly be configured such that they do not impact the use of the stethoscope as an acoustic stethoscope. In various embodiments, an electronic stethoscope may have an electrical component that converts vibrations into electrical signals instead of a drum and membrane of an acoustic stethoscope.

An electronic stethoscope as described herein may also include amplification circuitry operably coupled to the microphone and configured to amplify the electric signal generated by the microphone. The amplification circuitry may be part of the electronic stethoscope main unit 204, an external speaker module 206, or both. As just one example, amplification circuitry may be located within the electronic stethoscope main unit 204 and in the external speaker module at a final speaker amplifier stage 210.

A speaker 212 is operably coupled to the amplification circuitry (e.g., the final speaker amplifier stage 210) and configured to output the electric signal after amplification. In this way, the sound may be output for a user to hear. In FIG. 2, the speaker 212 is an external speaker that may be heard by anyone in the vicinity of the speaker 212, such as the patient themselves, the family of the patient, a healthcare professional, a healthcare student, and/or any other person. In various embodiments, the electronic stethoscope components 200 may include other or additional speaker types, such as wireless speakers or headphones, wired headphones, etc. Examples of different headphones are shown in and described below with respect to FIGS. 18A, 18B, and 19A-19C.

Figure 18A:
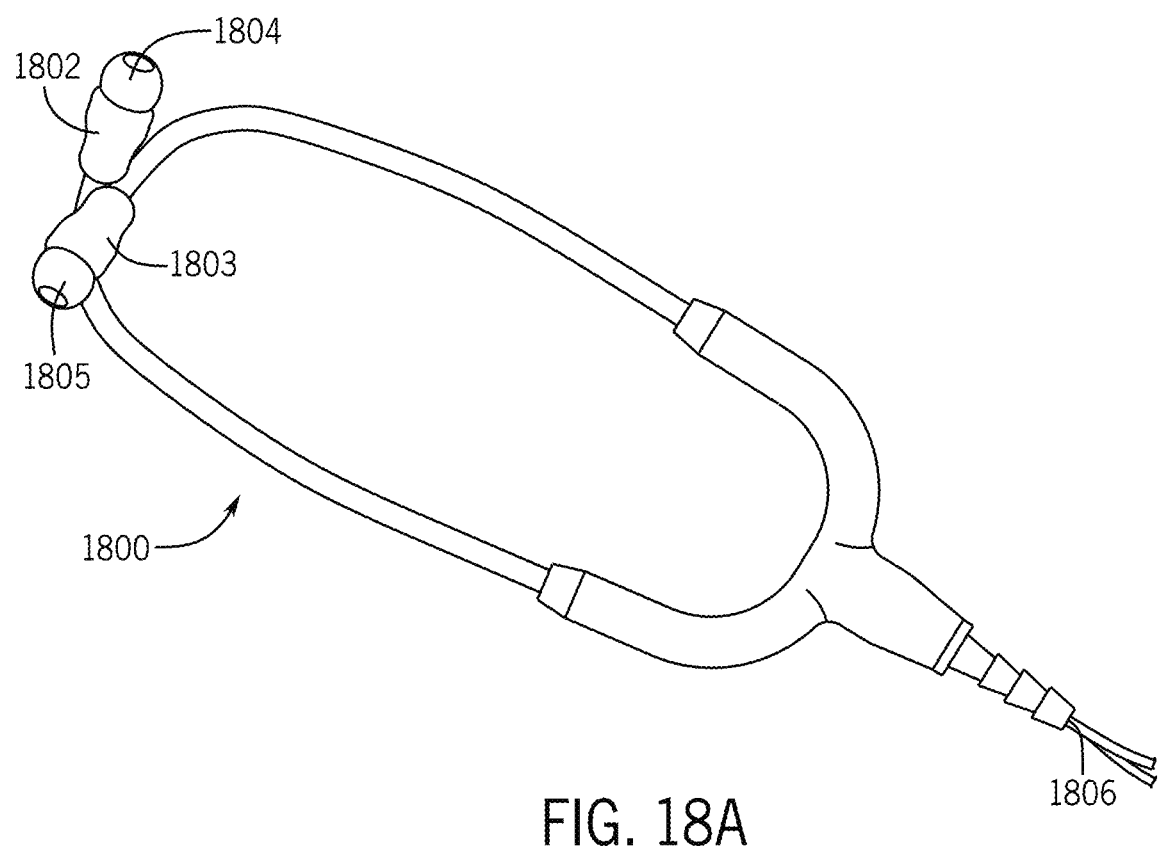
FIGS. 18A and 18B illustrate an electronic stethoscope with in-ear headphones according to some embodiments of the disclosure.
Figure 18B:
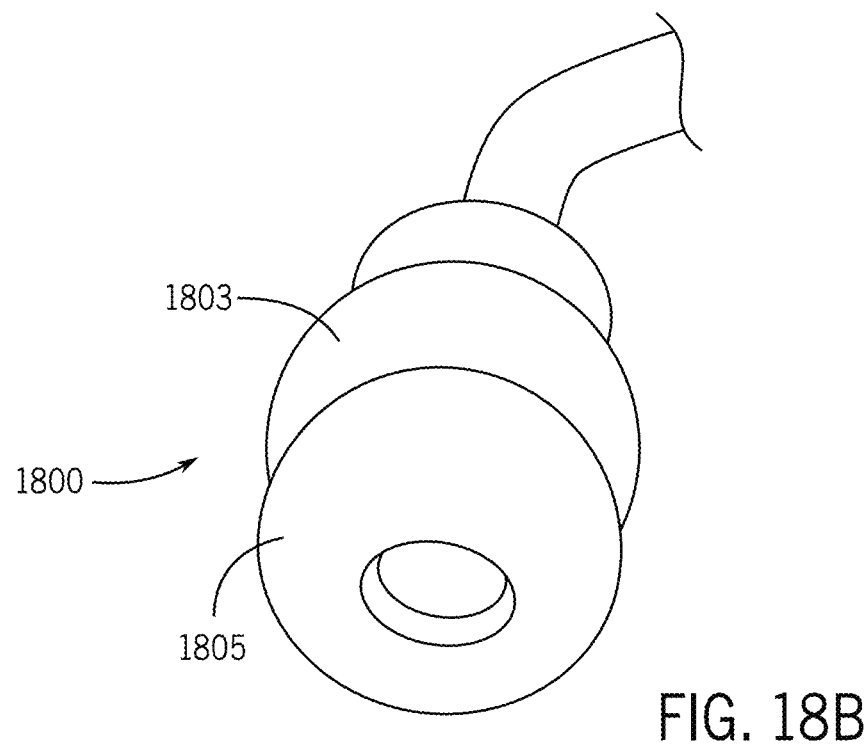

FIGS. 18A and 18B illustrate an electronic stethoscope 1800 with in-ear headphones according to some embodiments of the disclosure. In particular, the electronic stethoscope 1800 is an example of a stethoscope with headphones integrate into the stethoscope itself. For example, ear pieces 1802 and 1803 of the electronic stethoscope 1800 each include an in-ear earbud or headphone 1804 and 1805 that may be inserted into the ears of a user of the electronic stethoscope 1800. The earbuds 1804 and 1805 may be more comfortable than standard ear pieces of traditional stethoscopes, as they may be formed out of softer materials. A signal may be transmitted to the earbuds 1804 and 1805 through a wire 1806 so that audio may be output by the earbuds 1804 and 1805. In the electronic stethoscope 1800, the wire 1806 passes internally through the tubing of the electronic stethoscope. However, in various embodiments, wiring may be external to the tubing, integrated into a wall of the tubing, or a signal may be transmitted wirelessly to the earbuds 1804 and 1805 such that the wire 1806 or other wiring is not used. The earbuds 1804 and 1805 may be, for example, the speaker 212 of FIG. 2 or may receive a signal that is the same as or similar to the signal output to the speaker 212 of FIG. 2. If the earbuds 1804 and 1805 are configured to receive a wireless signal, the earbuds 1804 and 1805 may receive a wireless signal, for example, from a wireless module 306 of FIG. 3 (further described below). FIG. 18B shows an enlarged view of the ear piece 1803 and the earbud 1805 of the electronic stethoscope 1800.

Figure 19A:
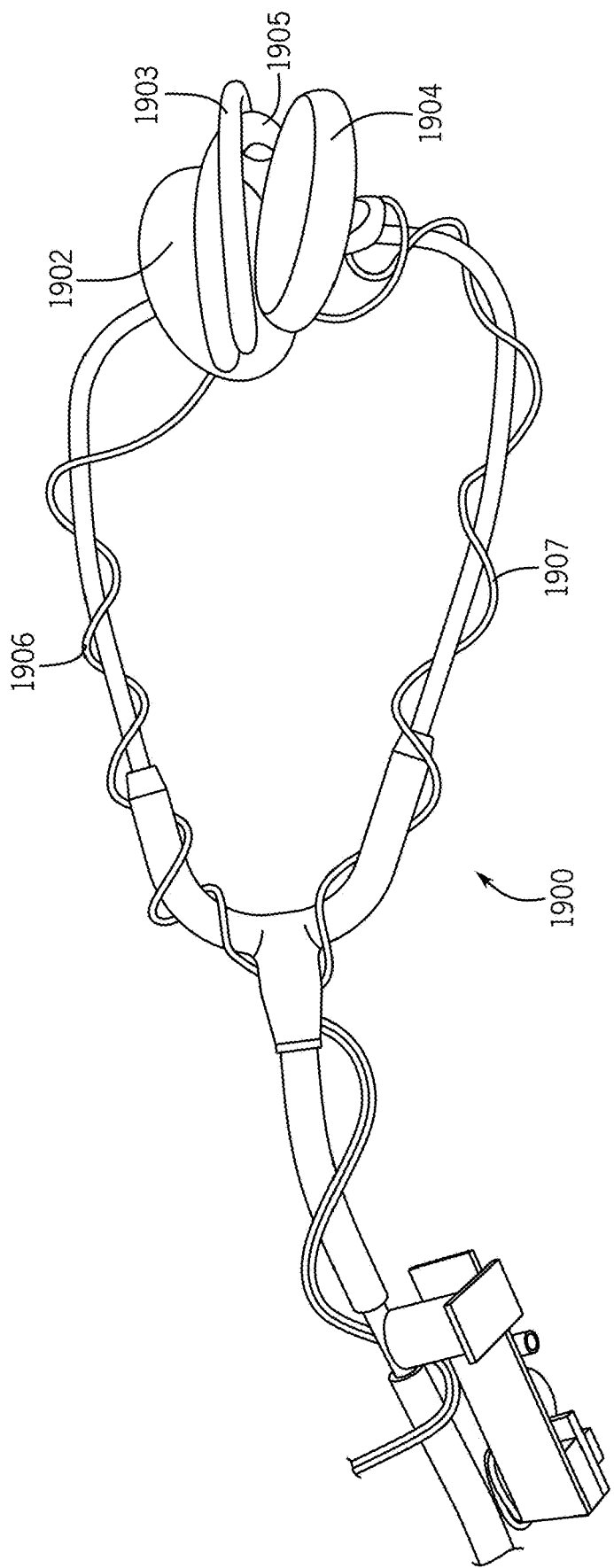
FIGS. 19A-19C illustrate an electronic stethoscope with over-ear headphones according to some embodiments of the disclosure.
Figure 19B:
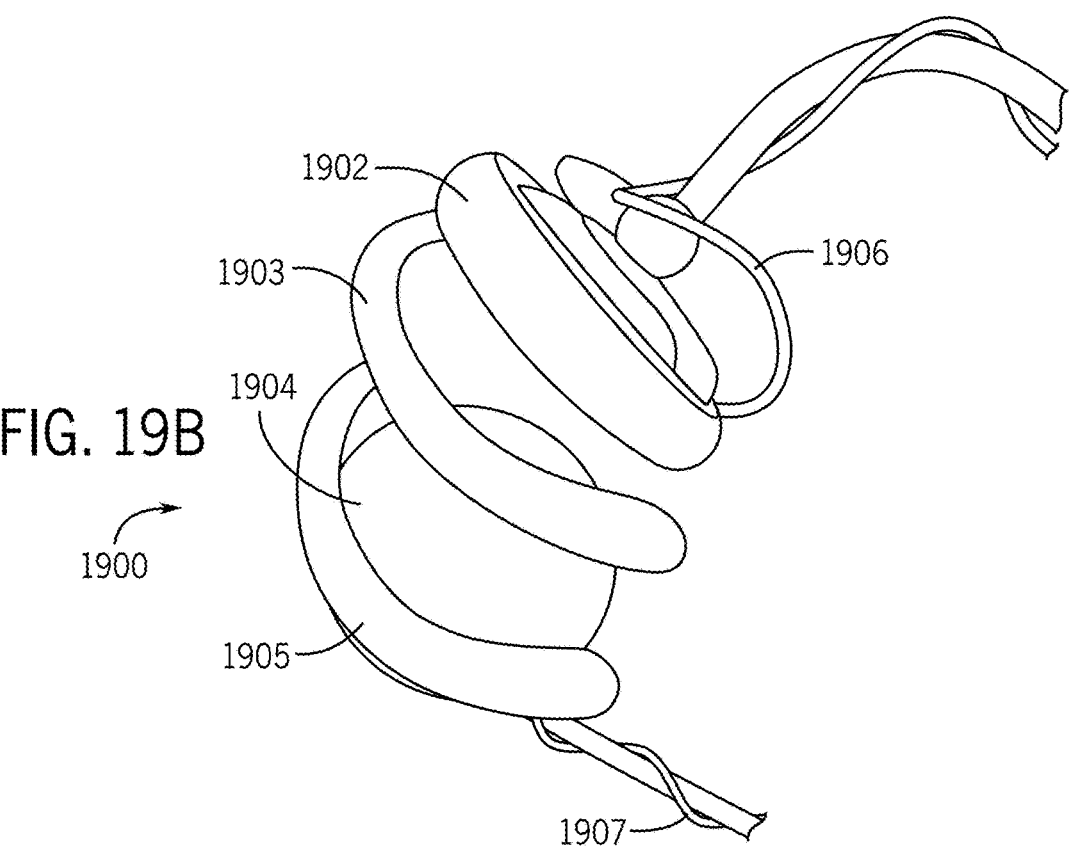
Figure 19C:
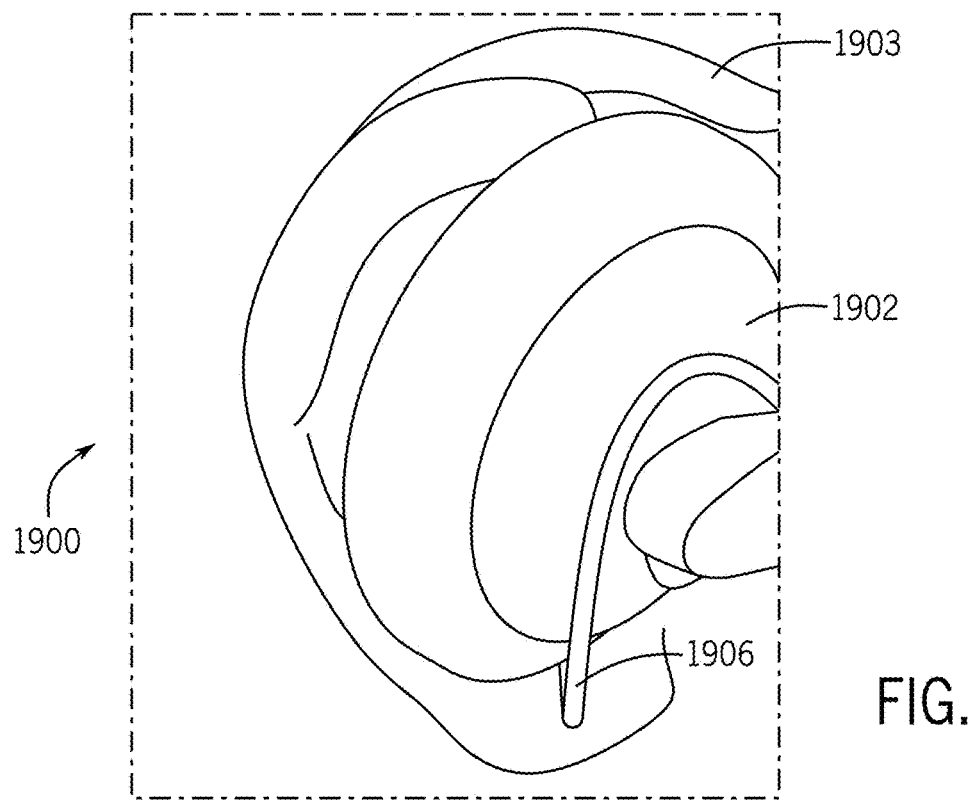

FIGS. 19A-19C illustrate an electronic stethoscope 1900 with over-ear headphones 1902 and 1904 according to some embodiments of the disclosure. The electronic stethoscope 1900 includes external wiring 1906 and 1907 to which audio signals may be transmitted to the headphones 1902 and 1904, respectively. Similar to the electronic stethoscope 1900 of FIGS. 18A and 18B, various embodiments using the headphones 1902 and 1904 may use internal wiring within the tubing, wiring integrated into the tubing wall, or may use wireless signals to transmit audio signals to the headphones 1902 and 1904. Each of the headphones 1902 and 1904 each includes a clip 1903 and 1905, respectively. The clips 1903 and 1905 allow a user to fit the headphones 1902 and 1904 over a user's ears, thereby securing both the headphones 1902 and 1904 and the electronic stethoscope to the user. The clips 1903 and 1905 are shown in more detail in FIG. 19B, and the headphone 1902 is shown attached to a user's ear using the clip 1903 in FIG. 19C.

FIGS. 18A, 18B, and 19A-19C show just two examples of speakers or headphones that may be implemented according to the various embodiments described herein to output audio with a speaker, headphone, etc. Other types of headphones, speakers, other audio output devices, or any combination thereof may be used to output an audio signal in various embodiments described herein. Headphones, such as those described in FIGS. 18A, 18B, and 19A-19C, may also be beneficial to a user from a comfort and ease of use standpoint when using the electronic stethoscopes described herein. For example, the ear pieces in standard stethoscopes are often hard and may be uncomfortable in a user's ears. Softer in-ear headphones or headphones that fit over and/or around a user's ears may relieve any pain or discomfort caused by hard ear pieces of traditional stethoscopes.

The external speaker module 206 also includes an external microphone 216 that picks up ambient noise and sound output by the speaker 212. A signal picked up by the microphone 216 is used by ambient noise cancellation signal processing 208 to filter ambient noise and/or sound output from the speaker 212 that may be picked up by the microphone of the electronic stethoscope main unit. This filtering may be done before the final speaker amplifier stage 210 to further reduce feedback from the speaker. The microphone 216 is considered external because it is not within the tubing, drum, bell, or ear pieces of the stethoscope and therefore does not directly pick up the acoustic signals detected using the diaphragm/drum or bell of the stethoscope. The ambient noise cancellation signal processing 208 may, in various embodiments, include other circuit components, such as other filtering and/or amplification components. Filtering/processing components of the electronic stethoscope may also cause the outputted signal to match or approximate a traditional acoustic stethoscope tube audio response. In this way, healthcare professionals may hear a similar sound to what an acoustic stethoscope would generate. In some embodiments, the signal outputted may match or approximate an acoustic stethoscope response. For example, the signal outputted may match the acoustic stethoscope output except for a magnitude or volume of the signal so that a healthcare professional could hear the output better. In another example, the signal processing may attempt to duplicate the acoustic stethoscope output except transpose the frequency of the output (e.g., lower a high frequency signal, raise a low frequency signal, move the output to a frequency band where there is less noise) to make it easier for a healthcare professional to hear the output.

The electronic stethoscope components 200 also include a power supply configured to power the amplification circuitry. The power supply may also power any signal processing components, the microphone, transceivers for wireless connectivity, etc. In FIG. 2, the external speaker module 206 is powered by a battery (not pictured). The power from the battery also supplies power to the electronic stethoscope main unit 204 through a powered input/output (I/O) connection. The external speaker module 206 also has a second powered I/O output 214 so that other devices, accessories, etc. as described herein may also be powered from the battery of the external speaker module 206 in a powered I/O daisy chain. Other devices, accessories, etc. may also be configured to have a battery with powered I/O connections. In various embodiments, some devices, accessories, etc. may not have a battery or other power source, but may receive power through a powered I/O connection for use by the device, accessory, etc. and may pass on power through a second powered I/O connection to other devices, accessories, etc. In this way, various devices may be interchangeable and/or used with the electronic stethoscope components 200 of FIG. 2. The various components, accessories, devices, etc. disclosed herein may be modular such that they may be removed from the stethoscope, interchanged for other devices/accessories, or compatible for other devices/accessories to be added. For example, aspects of the electronic stethoscope main unit 204 may be embedded in a stethoscope such that they are not easily removable from the stethoscope. However, a clipping mechanism of the electronic stethoscope main unit 204 may be connectable (through either a wired or wireless connection) to the external speaker module 206, such that connecting the two causes them to work together. Other accessories/devices may also connect to the electronic stethoscope main unit 204 in place of or in addition to the external speaker module.

Other configurations are also contemplated for the power supply. For example, a battery or other power source may be in the electronic stethoscope main unit 204 instead of or in addition to the external speaker module. In this way, the electronic stethoscope main unit 204 may be powered by its own power source or battery. The power source or battery of the electronic stethoscope main unit 204 may also power the external speaker module 206 when the two are connected, particularly if the external speaker module does not have its own power supply. The power from the battery of the electronic stethoscope main unit 204 may also pass through the external speaker module 206 to power other devices/accessories through the second powered I/O output 214. In various embodiments, a power supply may be some other supply than a battery, or may be a battery combined with some other supply. For example, a solar cell may provide power and/or charge a battery. As another example, the power supply may be a wall supplied power that the electronic stethoscope and/or accessory is plugged into.

In various embodiments, a power supply such as a battery may be a separate modular unit from other modular units such as the external speaker module 206. For example, a battery module may plug into the second powered I/O output 214 of the external speaker module 206 and power both the external speaker module 206 and the electronic stethoscope main unit 204. In various embodiments, a battery or other power supply may be insertable into various modules. For example, a battery may be part of the external speaker module 206, but may be removable for charging, replacement, etc. In various embodiments, the external speaker module may be plugged into a wall supplied power outlet to charge a battery of the external speaker module. In various embodiments, a battery may not be removable from a module. For example, a module may be disposable/replaceable such that the module is disposed of and/or replaced when it runs out of battery or after a predetermined number of uses (or after a single use). Accordingly, the power supply may be configured in various ways as described herein.

In various embodiments, an entire electronic stethoscope may be disposable and/or configured for single use. In medical contexts, many tools and other equipment is used only once so that the tool does not need to be sterilized after use, it may instead be disposed of In contexts where components of or an entire electronic stethoscope is configured for single use, components of the electronic stethoscope may be specifically configured for single use. For example, components may be less durable because the components must only be used once, battery life of batteries may be shorter as the battery needs to last only once, etc. For example, a coin cell or single AAA battery may be used in a disposable electronic stethoscope instead of a rechargeable battery or some other external power source. In another example, certain components may be made of plastic instead of metal (e.g., for an ear piece, headphone, clip, etc.). Components may also be designed such that they do not need to withstand typical sterilization procedures if the component or electronic stethoscope is only configured for a single use. For example, components may not need to be sealed as tightly to prevent ingress/egress of dust, fluid (air or liquid), etc. if the accessory or module is designed for a single use. Accordingly, components of and/or an entire electronic stethoscope as described herein may be configured for multiple or single (disposable) use. The packaging for a disposable electronic stethoscope may also vary as compared to a multiple use electronic stethoscope. Features of a disposable or single use electronic stethoscope may also be designed to be less complex. For example, software of a single use may be configured to provide for less features than a multiple use electronic stethoscope. For example, instead of providing a continuum of volume settings using touch sensitive buttons, a predetermined number of discreet volume levels or a single volume level may be used to reduce the complexity of both the software and/or hardware used in a single use electronic stethoscope. An automatic gain circuit that provides automatic volume control based on conditions (e.g., ambient noise levels) may also be used in an electronic stethoscope. That automatic gain circuit may be used in lieu of manual volume controls in a single use electronic stethoscope to reduce complexity. In some embodiments, the automatic gain circuit may be used in multiple use electronic stethoscopes along with a manual control aspect, and the automatic gain circuit may be eliminated in a single use stethoscope in favor of manual controls to reduce complexity in the single use electronic stethoscope.

The second powered I/O output 214 may also provide data output from the external speaker module 206. For example, the signal from the electronic stethoscope main unit 204 (before and/or after processing at the ambient noise cancellation signal processing 208 and/or final speaker amplifier stage 210) may also be output through the second powered I/O output 214. This output may go to a computer/database/server for storage, further analysis/processing, a remote telemedicine healthcare provider, etc. The output may also be sent to other modules, such as a wireless transceiver, advanced filtering circuitry, or any other type of modular device. In various embodiments, the electronic stethoscope main unit 204 and/or the external speaker module may provide additional connectors/ports (either wired or wireless) for additional listeners, headphones, remote listening devices (e.g., not in the same room as the living subject), etc. Outputs to additional listeners may be helpful in a teaching environment, where it is helpful for multiple students, residents, etc. to hear an output from an electronic stethoscope or other module described herein. Outputs to additional listeners may also be valuable for remote or telemedicine care. Outputs may also be to a speaker, e.g., mounted in a classroom or other room, so that multiple listeners can hear the output. If an external speaker is in the same room where the electronic stethoscope is used, the audio processing of the electronic stethoscope may filter out noise and/or feedback from the external speaker.

Various electronic stethoscope components and/or modules may also be configured such that a device is powered off (e.g., power is not used) when a module is not present. This may conserve battery. For example, assume the electronic stethoscope main unit 204 has a battery. If an external speaker module 206 (or some other module) is not plugged into the electronic stethoscope main unit 204, the electronic stethoscope main unit 204 will logically or physically switch off the electrical components (or some of the electrical components) of the electronic stethoscope main unit 204 such that those components do not draw power from the battery, conserving the battery's life. This may be accomplished with a sensor to determine if something is plugged in (e.g., whether a headphone jack/port is plugged in or not). If a presence of a headphone connector is not sensed, the device will turn off. Similarly, the components of the stethoscope may determine whether a wireless module, such as a headphone or speaker are connected. If not, the device will turn off. If so, the device powers on. In various embodiments, a module (e.g., the electronic stethoscope main unit 204, the external speaker module) may also have a power switch that may be turned on and off by a user. For example, various embodiments of the light accessory/module described herein may have a switch that turns the light on and off, helping preserve battery life.

In various embodiments, modules and/or accessories may also go into a sleep and/or standby mode to reduce power consumption from a battery or other power source. For example, in a light accessory or other accessory or module with a user input functionality may be programmed to go into a sleep and/or standby mode when the user input (e.g., on/off switch of a light accessory) has not been actuated for a predetermined period of time. For example, touch sensitive user inputs may use larger amounts of power to be responsive to touch and subtle changes in a user's touch. As described herein, touch sensitive inputs may be used to adjust a brightness and/or focus of a light, for example. If a standby or sleep mode is entered into after a predetermined amount of time with no input, a light accessory for example may cease tracking the touch sensitive aspects of the input or may reduce the sensitivity of responsiveness touch sensitive aspects of the input. Then, when an input that requires less power to detect (e.g., user input through an on/off switch, strong touch to a reduced responsiveness touch sensor) is received by the accessory it may "wake up" and transition back into a mode where it is more sensitive and/or responsive. In this way, battery life may be preserved by not powering certain aspects of an accessory or module that draw more power than other user input aspects until some input is received indicating that the accessory or module is being actively used.

In various embodiments, other methods and electrical components may be used to determine whether a device is in use or not. For example, a module or electronic stethoscope component may include a motion sensor, accelerometer, or the like to determine whether the module/stethoscope is motion and therefore likely being used. If so, the module and/or electronic stethoscope components may be powered on. If the motion stops, or stops for a predetermined amount/threshold of time, the module and/or electronic stethoscope components may be turned off automatically by the system. In other words, sensors may be used to determine whether an electronic stethoscope is in use. When it is in use, power is provided to the amplification circuitry, for example. When it is not in use power is not provided to the amplification circuitry, for example. Other sensor types than motion sensors may also be used. For example, any other type of light, heat, touch, or other type of sensor may be used to activate or turn on a device or determine whether it is likely in use. For example, if a light sensor senses that a light in a room is on, the electronic components may be on or active assuming that the electronic stethoscope is being used or may be in use soon, but deactivate while the light sensor senses darkness. Other sensor types may be used in a similar fashion to determine whether an electronic stethoscope or component thereof is in use or likely to be in use in order to control power consumption of the electronic stethoscope or components thereof.

In another example, the determination whether an electronic stethoscope is in use or not is made may be based on an amplitude of the electrical signal generated by the microphone is below a predetermined threshold. That is, if the sound sensed by the microphone is loud enough or of a high enough magnitude, the device will be considered in use and will turn on. In this way, the device will power down, for example, if it is just sitting in a room alone, but will switch on when people walk in talking or the stethoscope is handled such that the microphone picks up noise of a predetermined magnitude. The stethoscope may further be configured to turn on if the noise lasts for a predetermined amount of time.

Figure 3:
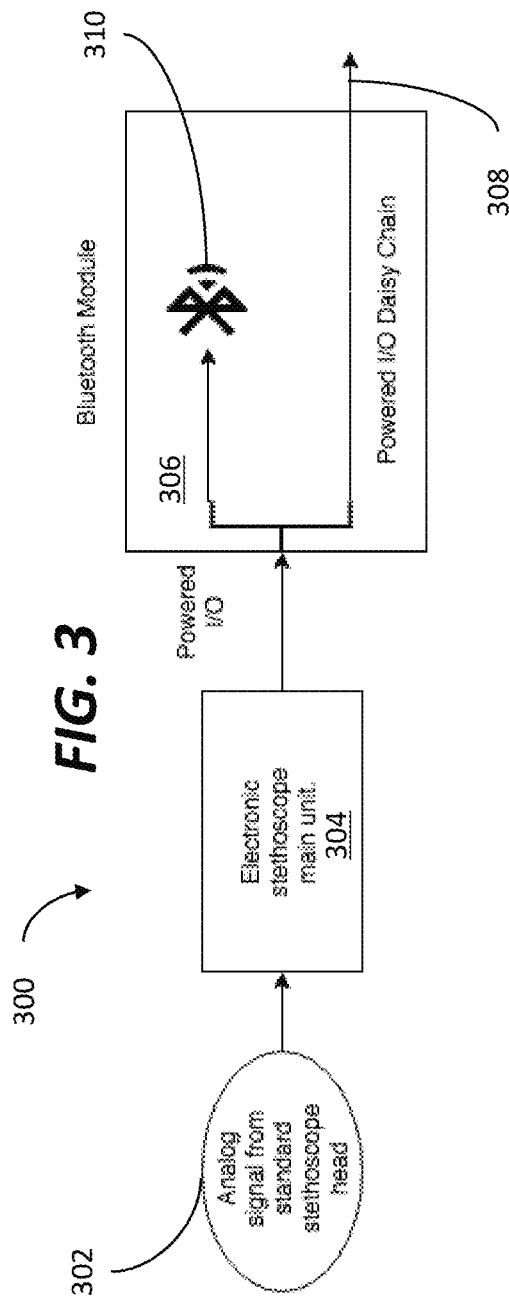
FIG. 3 is a schematic diagram of electronic stethoscope components with a wireless module according to some embodiments of the disclosure.

FIG. 3 is a schematic diagram of electronic stethoscope components 300 with a wireless module 306 according to some embodiments of the disclosure. The electronic stethoscope components 300 of FIG. 3 include an analog signal from a standard stethoscope head 302, which may be similar to the analog signal from a standard stethoscope head 202 of FIG. 2. The electronic stethoscope components 300 also include an electronic stethoscope main unit 304, which may be similar to the electronic stethoscope main unit 204 of FIG. 2.

The wireless module 306 is connected to the electronic stethoscope main unit 304 through a powered I/O connection similar to the powered I/O connections described herein with respect to FIG. 2. Accordingly, the wireless module 306 may transmit and/or receive power through its powered I/O connections, including to and/or from the electronic stethoscope main unit 304 and/or any other module connected through a second powered I/O output 308. In this way, various modules may be powered by a power supply of the electronic stethoscope main unit 304, the wireless module 306, or other power supply as described herein.

The wireless module 306 in FIG. 3 is a Bluetooth wireless module, but in various embodiments other wireless protocols may be used. The wireless module 306 may include electronic components such as a wireless connection port 310. Various devices may connect to the wireless module 306 through the wireless connection port 310. For example, wireless headphones may be connected to the wireless module 306 so that the output from the stethoscope may listened to. A computing device such as a smartphone may also connect wirelessly to the wireless module 306. Audio may be output to the smartphone through the connection to be saved, analyzed, further processed, transmitted to other computing devices, transmitted/output to speakers and/or headphones, etc.

Other modules than those shown in FIGS. 2 and 3 are also contemplated herein. For example, advanced audio processing modules may be utilized to further process, filter, or analyze the audio signal picked up by an audio sensor in the stethoscope. For example, ambient noise cancelling may also be used in the embodiment of FIG. 3. Other modules may include diagnostic tools, such as a display that visually represents audio signals picked up by the stethoscope. In addition, the modules disclosed herein, including audio modules such as those shown in FIGS. 2 and 3 may also be integrated into or removable from an electronic stethoscope. Where a module is integrated into the electronic stethoscope, the module is not easily removable from the electronic stethoscope by the user. In such embodiments, the modules may come pre-assembled and packaged to look similar to a traditional stethoscope, as the circuitry or other portions of the modules may be integrated into the hardware of a stethoscope itself.

Figure 4:
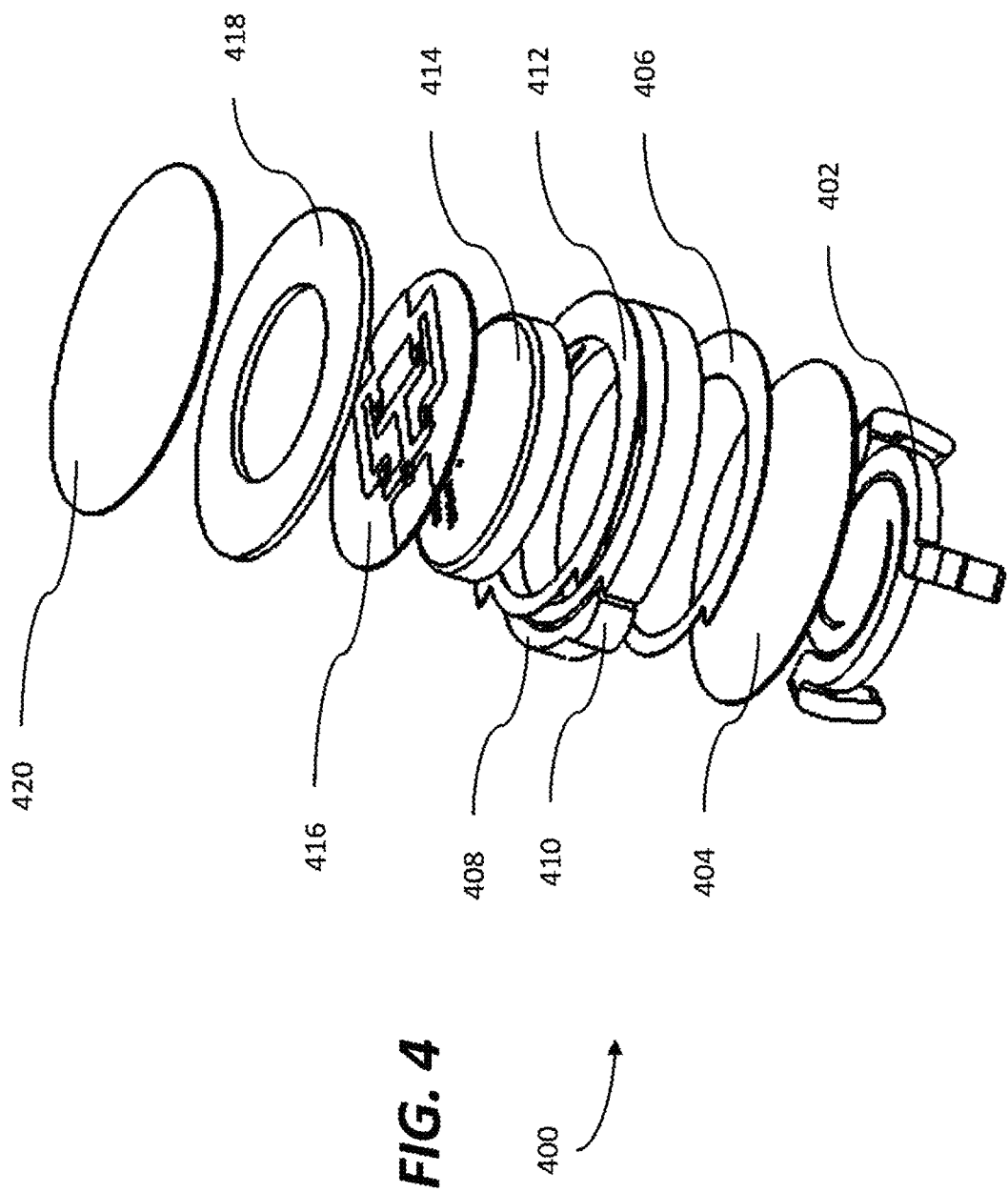
FIG. 4 illustrates a light accessory for a stethoscope according to some embodiments of the disclosure.

As another example of a module that may be used in conjunction with a stethoscope (either electronic or acoustic), FIG. 4 illustrates a light accessory 400 for a stethoscope according to some embodiments of the disclosure. FIG. 4 shows example components of a light accessory, but additional, fewer, or different components may be used in other light accessories. The light accessory includes a mount 402 that is used to removably attach the light accessory 400 to a stethoscope. The mount 402 is a type of clipping mechanism configured to connect the light accessory to a stethoscope. Various clipping mechanisms are possible and some examples are shown in FIGS. 5, 6A, 6B, 7A-7D, and 8A-8D. The mount 402 is configured to attach around the outside a bell of a stethoscope, such as the bell 164 of the stethoscope 160 of FIG. 1. By attaching the light accessory 400 to the bell of a stethoscope, the diaphragm of the stethoscope may still be used while the light accessory 400 is attached. Additionally, the bell/drum of a stethoscope end is easily held and handled by one hand of a healthcare professional. When the light accessory 400 is attached to the drum/bell of the stethoscope, the light accessory 400 can also therefore be easily handled with the same hand without use of a second hand, without having to switch instruments, etc. For example, if a healthcare professional is using the diaphragm portion of the stethoscope, the healthcare professional merely flips the drum/bell portion around to use the light attached to the bell. The light accessory 400 also includes a switch 410 to turn the light on and off. This switch 410 may also be manipulated by that same hand to turn the light on and off, advantageously providing convenience and ease of use to the healthcare professional.

As described herein, the light accessory 400 attaches to the bell of a stethoscope via the mount 402. The mount 402 may be configured to fit various sizes of stethoscope bells. For example, the mount 402 may be made from a flexible rubberized plastic that can bend to fit many different sizes and shapes of stethoscope. This provides a snug fit that will prevent the light accessory 400 from moving on the bell when the stethoscope is being used. Rubberized material may also provide dampening between the stethoscope and the light accessory 400. This advantageously helps prevent additional noise being transmitted into the stethoscope. For example, a switching mechanism such as the switch 410 may produce a clicking noise when the light accessory 400 is turned on and off. The rubberized material absorbs some of that noise preventing it from being too loud for someone wearing the stethoscope. In another example, attaching or removing the mount 402 and light accessory 400 from the stethoscope may produce noise, but the rubberized material again helps prevent that noise from being transmitted into the stethoscope. Where the light accessory 400 is used with electronic filtering components, those components may also filter out noise from a switch and/or attaching/detaching the light accessory 400 from the stethoscope.

In various embodiments, other types of mounts may be utilized that attach the light accessory 400 to a stethoscope in other ways and/or or onto other portions of a stethoscope. For example, a mount may be a clip that attaches the light to tubing of a stethoscope, or attaches the light to the portion between the bell and the drum such that neither of the bell or diaphragm are blocked from use while the light is attached.

Attached to the mount 402 is a cover 404 of the light accessory 400. The cover may have an adhesive to attach it to the mount 402. An adhesive layer 406 attaches the cover 404 to a spacer 408 with the built-in switch 410 that is used to turn the light accessory on and off. Advantageously, the switch 410 is accessible to the user while the light accessory 400 is clipped to a stethoscope. A battery 414 fits into the space within the spacer 408, and an adhesive layer 412 attaches a circuit board 416 to the spacer 408 opposite the cover 404. The spacer 408, the battery 414, and the circuit board 416 are sized and configured to fit together such that the circuit board 416 has leads that electrically connect the circuit board 416 with the battery 414 when the switch 410 is in the on position. In this way, a light mounted on a surface of the circuit board 416 opposite the battery 414 may be powered on when the switch 410 is in the on position. A second spacer 418 fits over the circuit board 416, but is hollow in the middle to allow light from the circuit board 416 to shine through. The spacer 418 also has adhesive to allow a cover 420 to attach to it. The cover 420 is transparent or at least translucent to allow light from the circuit board 416 to shine through. The light may be, for example, a light emitting diode (LED) or any other kind of light.

The light may have additional components that allow a user to adjust light direction, intensity, etc. Adjusting the light direction, intensity, etc. may affect battery life, how often the battery must be replaced, charged etc. Advantageously, having an adjustable light makes for more efficient use in different ambient lighting conditions, for different clinical purposes (e.g., examining nose, throat, ear, etc.). The light may be adjusted or configured to focus on a desired region, have a particular uniform or non-uniform intensity, have a particular color temperature, etc.

FIG. 4 shows a battery stored directly in the light accessory 400. However, in various embodiments, the battery may be stored in a different portion of the stethoscope or in a different module attachable to the stethoscope and/or the light accessory 400 as described herein (e.g., through a daisy chained powered I/O connection). In various embodiments, the light accessory 400 may also be connected through an electrical wired connection to any other type of power supply, including a battery in a different module, a wall supplied power, etc. In various embodiments where the battery is in the light accessory 400, other modules or electronic components of a stethoscope may connect to or plug into the light accessory 400 to be powered by the battery 414 of the light accessory 400.

The battery 414 may also be removable from the light accessory 400 such that the battery 414 is changeable when the battery 414 dies, or so that the battery 414 may be removed to be charged. In various embodiments, the battery 414 may also be non-removable from the light apparatus. In such embodiments, the light accessory 400 may be configured such that the battery 414 is rechargeable while in the light accessory 400 (e.g., through wired or wireless charging). In various embodiments, the battery 414 may not be rechargeable, but is instead designed to be disposed of along with the light accessory 400 after the battery 414 dies and/or after a predetermined number of uses (e.g., in sterile or high-risk environments the light accessory 400 may only be used once and then disposed of to protect patients from contamination).

Figure 14A:
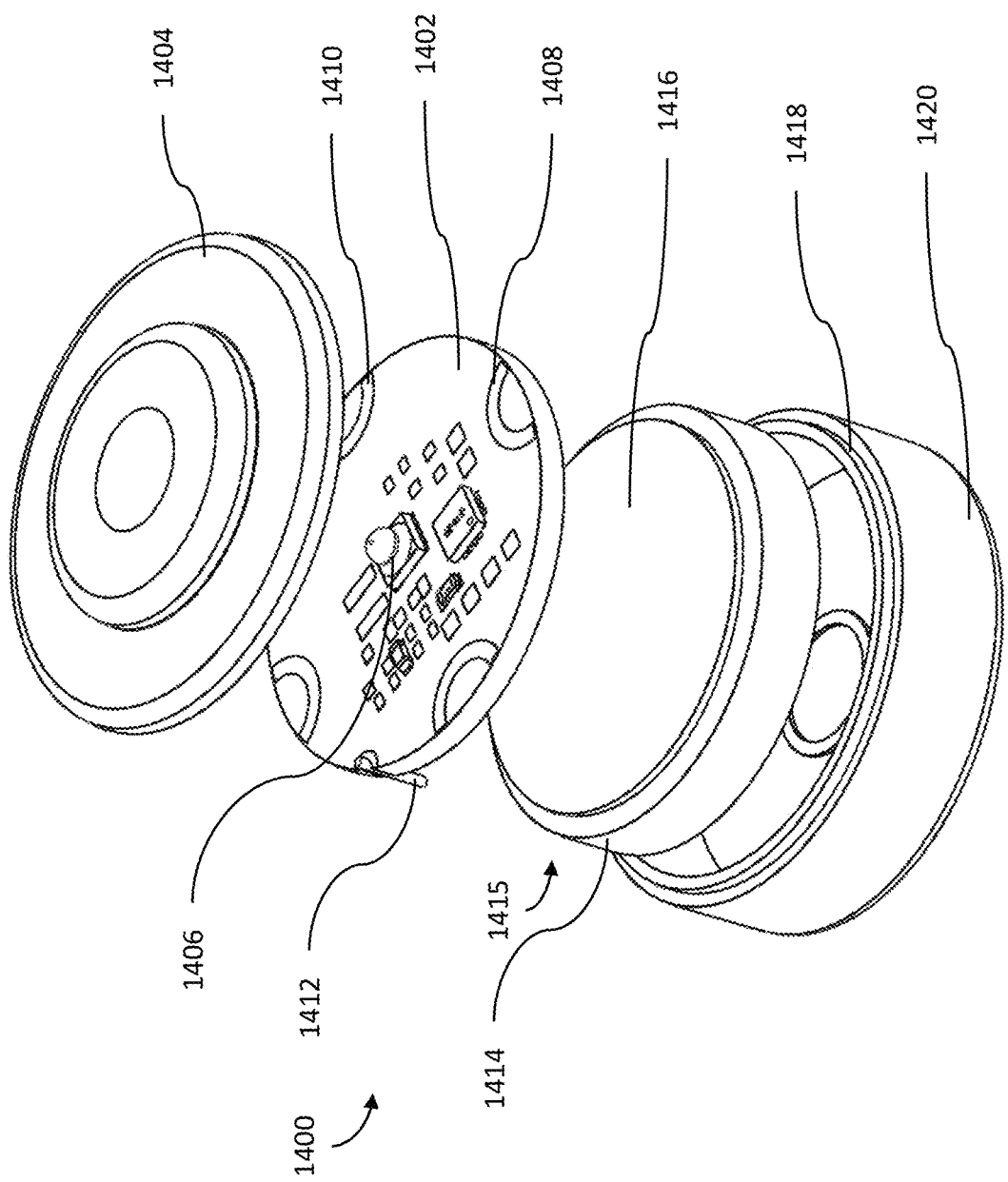
FIGS. 14A and 14B illustrate another example of a light accessory according to some embodiments of the disclosure.
Figure 14B:
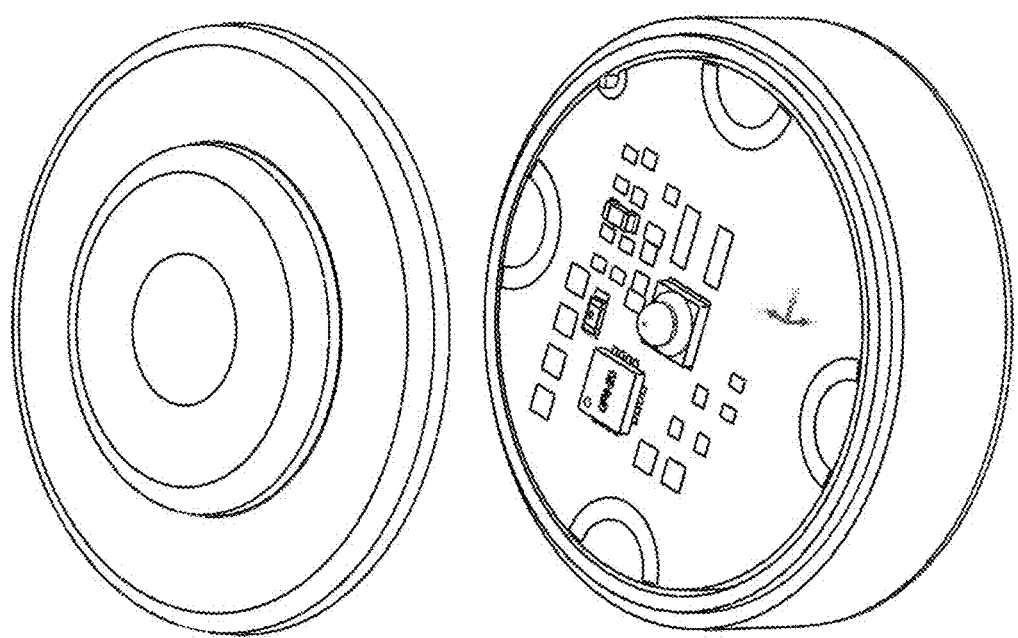

FIGS. 14A and 14B illustrate another example of a light accessory 1400 according to some embodiments of the disclosure. FIG. 14A illustrates an exploded view of the light accessory 1400. The light accessory 1400 includes a cover 1404 with a lens, a circuit board 1402, a battery 1415, and a base 1420. The battery 1415 sits within a recess of the base 1420. In particular a positive contact 1414 portion of the battery 1415 rests within the base 1420. Only a top edge of the positive contact 1414 portion of the battery 1415 is exposed while the battery 1415 rests within the base 1420. The top edge of the positive contact 1414 portion of the battery 1415 surrounds a battery negative 1416 surface of the battery 1415. The battery 1415 of FIG. 14A is larger with respect to the rest of the light accessory 1400 than the battery 414 of FIG. 4.

The circuit board 1402 sits on top of the battery 1415, such that contacts on the underside of the circuit board 1402 (not shown) electrically connect with the battery negative 1416 surface of the battery 1415. A positive contact 1412 attached to the circuit board 1402 extends down away from the circuit board 1402 to electrically connect with the positive contact 1414 portion of the battery 1415. In this way, the circuit board 1402 may be electrically connected with the positive and negative of the battery 1415 to power the circuit and an LED 1406.

The circuit board 1402 may include one or more touch sensors such that the light assembly may use a touch sensitive button to turn the LED 1406 on and off. The touch sensors in FIG. 14A are represented by four semi-circle shaped circuit components at the edge of the circuit board 1402. For example, touch sensors 1408 and 1410 are shown in FIG. 14A. The touch sensors may be, for example, capacitive sensors, such that when a user places a finger near the touch sensors, the touch sensors will pick up the presence of the user's finger. In this way, the touch sensors may cause the LED 1406 to be controlled (e.g., turn on/off, adjust/control brightness, etc.). A microprocessor on the circuit board 1402 may be used in combination with the touch sensors. The microprocessor may include RC oscillators used to sense a baseline capacitance, and when a finger is brought in contact with or near the touch sensitive features at the edge of the circuit board 1402, the capacitance of those features may increase and the oscillators may then change in frequency. If the frequency changes more than a predetermined threshold, the microprocessor may determine that the sensor is being touched. Other types of touch sensors and/or switches may be used to control the LED 1406 according to various embodiments. In various embodiments, the touch sensors may be positioned or configured such that the sensors detect a presence of a user's finger when it is located on the side of the base 1420, above the cover 1404, or both.

The circuit board 1402 may also be part of a mechanical system that provides pressure on the battery contacts (the positive contact 1414 and the battery negative 1416 surface) via an elastic spring force of the plastic of the cover 1404 and the base 1420. The cover 1404 may compressed onto the base 1420, for example during a sonic welding process. In various embodiments, a sonic welding process may also join the circuit board 1402 and/or the touch sensors to the base 1420 and/or the cover 1404. The sonic welding may be utilized to provide a hermetic seal of the light accessory 1400. This sealing protects the components inside the base 1420 and the cover 1404 (e.g., the circuit board 1402, the battery 1415, the LED 1406, the touch sensors, etc.), preventing liquid, dust, etc. ingress and/or egress into or out of the light accessory 1400. This also makes the light accessory easier to sterilize than if the cover 1404 and the base 1420 were not adequately sealed. The seal, thereby, gives the health care provider total freedom to handle and utilize the light accessory 1400, even with contaminated gloves, knowing that the light accessory 1400 can be appropriately sterilized and re-used at a later time, regardless of use in the highest of contamination or infectious risk situations (e.g. management during an Ebola infection/outbreak). In various embodiments, the plastic components of the light accessory 1400 may be made of biodegradable material, such as biodegradable plastic.

The cover 1404 may also act as a lens for the LED 1406. A cross-section of an example lens is shown in and described below with respect to FIG. 15A. The lens of the cover 1404 may be, for example, concave in shape so that the light from the LED 1406 is focused into a beam, such that light from the LED 1406 is concentrated into a narrower region than the light would be otherwise. The lens of the cover 1404 may be configured in various embodiments to have different fields of illumination and/or concentration/brightness of the light. In various embodiments, a lens may be adjustable so that a user may adjust the field of illumination and/or concentration/brightness of the light as desired. Other light guiding shapes may be used in a lens. For example, an LED may be at a different location on the top of the circuit board 1402 instead of in the center of the circuit board 1402 as shown in FIG. 14A. An LED may also be located on a side of the circuit board 1402, for example. In various examples, the lens may be configured to allow light to shine out the top of the light accessory 1400 and/or the side as desired. For example, the base 1420 may have a transparent side so that light may be emitted from the side of the light accessory 1400. Since plastic has a different permeability than air, the properties of Snell's law may be utilized to cause a desired pattern of light by adjusting the light accessory 1400's optical geometry.

FIG. 14B additionally shows the light accessory 1400 of FIG. 14A where the circuit board 1402, the battery 1415, and the base 1420 are assembled and the cover 1404 is shown exploded/unassembled.

FIG. 15A illustrates a cross-sectional perspective view of a cover 1550 of the example light accessory 1400 of FIGS. 14A and 14B according to some embodiments of the disclosure. For example, the cover 1550 may be the cover 1404 of the light accessory 1400 of FIG. 14A. The cover 1550 includes a lens region 1566. The lens region 1566 is configured to direct light from a light source in a particular direction as described herein. The lens region 1566 may be shaped in different shapes to focus light from a light source in different ways, such as providing more or less focus, focus in a particular direction, etc. The lens region 1566 in the example of FIG. 15A is a convex lens shape to focus the light toward a particular focal point.

The cover 1550 also includes a space 1558 with an edge 1556 configured to fit around the edges of a circuit board, such as the circuit board 1402 of FIG. 14A. The space 1558 may be configured such that the edges of the circuit board are securely held by the edge 1556 of the cover 1550, for example through a compression fit.

The cover 1550 also includes a space 1554 configured to fit around an edge of a base, such as the base 1420 of FIG. 14A. The cover 1550 and base may be configured such that there is a compression fit between an edge 1552 and the edge of the base. In addition, as disclosed herein, the cover 1550 at the edge 1552 and the base may be sonic welded together, or otherwise joined in a manner that hermetically seals the cover 1550 at the edge 1552 to the base.

The cover 1550 includes a portion 1560 that extends radially around the cover 1550 and, when assembled, sits on top an outer radial portion for the circuit board. A raised portion 1564 toward the center of the cover 1550 with respect to the portion 1560 creates a space 1562. The space 1562 may provide room, for example, for components on the circuit board, such as a light source (e.g., an LED). In addition, where touch sensors are used (e.g., as in FIGS. 14A and 14B), the portion 1560 provides a natural surface for a user to moved their finger along, which is bounded by the raised portion 1564 so that the user may easily slide their finger around a perimeter of the cover 1550. Furthermore, in an example embodiment, a lower surface of the portion 1560 is in contact with the circuit board of a light accessory (e.g., the bottom plane of the portion 1560 rests upon touch sensitive circuit elements). Accordingly, the cover 1550 and/or the portion 1560 then comprise physical parts of a capacitor in a capacitive sensing circuit. The capacitance of such a capacitive sensing circuit varies when a finger of a user, for example comes in proximity to or in contact with the cover 1550 in the region above the touch sensitive circuit elements on the circuit board (e.g., the region of the portion 1560).

Figure 15B:
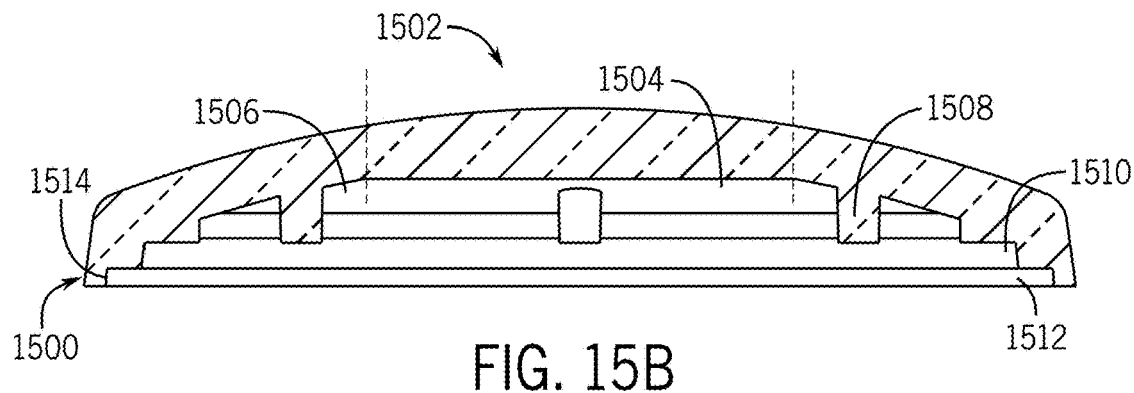
FIG. 15B illustrates a cross sectional view of another embodiment of a cover of a light accessory according to some embodiments of the disclosure.

FIG. 15B illustrates a cross sectional view of another embodiment of a cover 1500 of a light accessory according to some embodiments of the disclosure. The cover 1500 includes a lens region 1502 between lens region boundaries 1504 and 1506. The lens region 1502 is configured to direct light from a light source in a particular direction as described herein. The lens region 1502 may be shaped in different shapes to focus light from a light source in different ways, such as providing more or less focus, focus in a particular direction, etc.

The cover 1500 also includes a space 1510 configured to fit around the edges of a circuit board, such as the circuit board 1402 of FIG. 14A. The space 1510 may be configured such that the edges of the circuit board are securely held by the cover 1500, for example through a compression fit. Structural pins, including for example structural pin 1508, are also included in the cover 1500. The structural pins contact portions of the circuit board to also help hold the circuit board in place. In addition, the structural pins may contact portions of the circuit board in locations that do not block a portion of the surface that emits light, and may also contact the circuit board in locations that do not have sensitive circuitry. The structural pins may also prevent the cover 1500 from deforming from contact from a user such that portions of the cover other than the structural pins contact the surface of the circuit board.

The cover 1500 also includes a space 1512 configured to fit around an edge of a base, such as the base 1420 of FIG. 14A. The cover 1500 and base may be configured such that there is a compression fit between an edge 1514 and the edge of the base. In addition, as disclosed herein, the cover 1500 at the edge 1514 and the base may be sonic welded together, or otherwise joined in a manner that hermetically seals the cover 1500 at the edge 1514 to the base.

Figure 16:
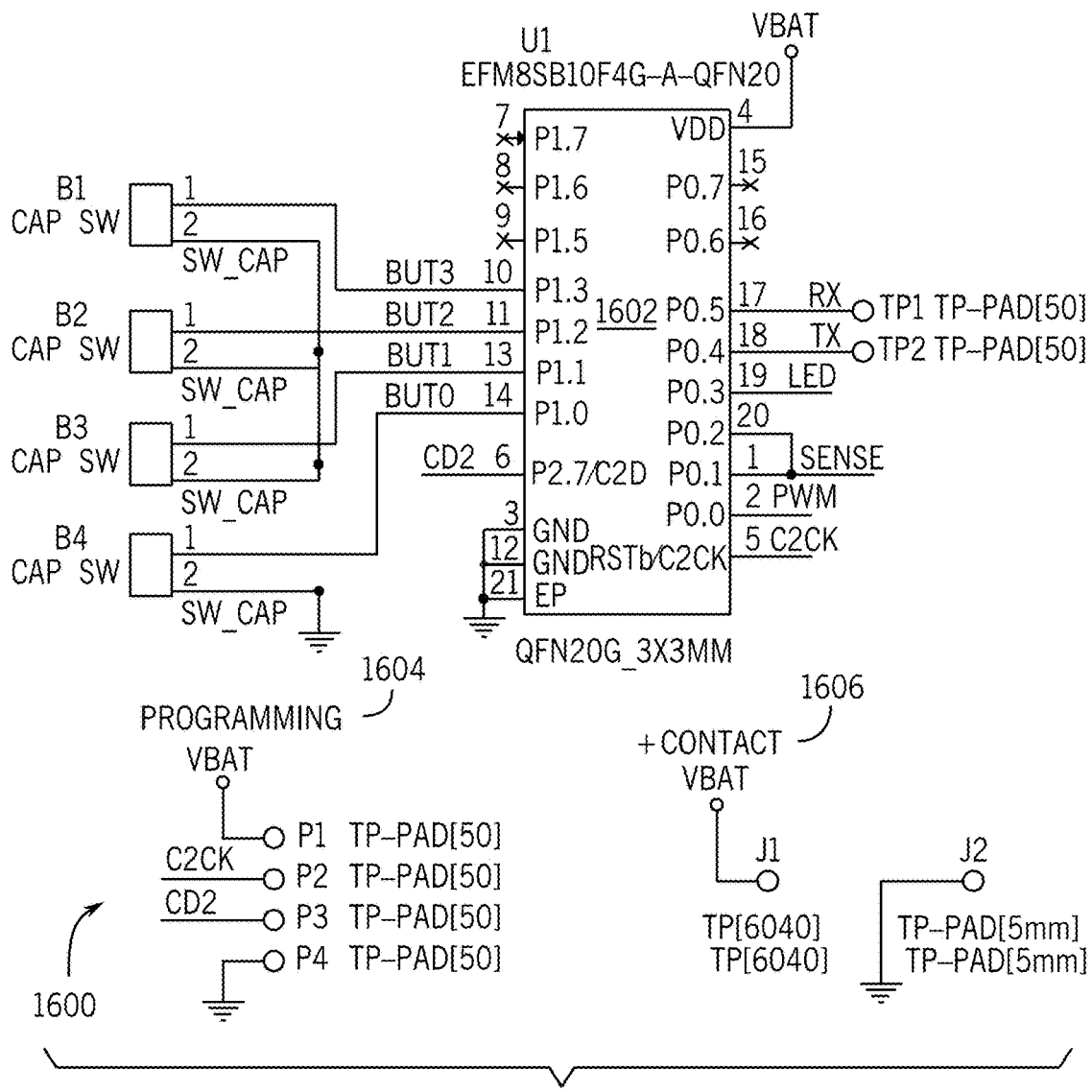
FIG. 16 illustrates a circuit schematic of an example light accessory according to some embodiments of the disclosure.

FIG. 16 illustrates a schematic of a circuit 1600 of an example light accessory according to some embodiments of the disclosure. The circuit 1600 may exist on, for example, the circuit board 1402 of FIG. 14A. The circuit 1600 connects a battery, such as the battery 1415 of FIG. 14A to touch sensors, such as the touch sensors 1408 and 1410 of FIG. 14A, so that the touch sensors may be used to turn a light source, such as the LED 1406 of FIG. 14A, on/off and/or adjust the LED. In the circuit 1600, the touch sensors are shown as buttons B1, B2, B3, and B4. Each of the buttons B1, B2, B3, and B4 are connected to ground and to a microprocessor 1602 at pins 10, 11, 13, and 14 respectively. The microprocessor 1602, may be, for example, an EFM8SB10F4G-A-QFN20 microprocessor chip.

A programming portion 1604 of the circuit 1600 shows leads for a test point for programming the touch sensors (e.g., buttons B1, B2, B3, and B4). In other words, the programming portion 1604 of the circuit 1600 provides a way to adjust how inputs from the touch sensors cause the microprocessor 1602 to control an LED connected at pin 19 (e.g., to turn on/off and/or adjust the LED). P1 of the programming portion 1604 is connected to a positive terminal of a voltage source, such as a battery and P4 is connected to ground. P2 of the programming portion 1604 is connected to pin 5 of the microprocessor 1602 and P3 is connected pin 6 of the microprocessor 1602. Accordingly, these leads P1-P4 may be connected to in order to program the microprocessor 1602 to control the LED.

Pin 4 of the microprocessor 1602 is also connected to the positive terminal of a voltage source, such as a battery, while pins 3, 12, and 21 of the microprocessor 1602 are connected to ground. Pins 1 and 20 of the microprocessor 1602 may be optionally connected to a step up circuit, which is shown in and described with respect to FIG. 17. Similarly, pin 2 may also be optionally connected to the step up circuit as shown in and described with respect to FIG. 17. Pins 17 and 18 may be test points that may be soldered to in order to test outputs of the microprocessor 1602. Such outputs may be used, for example, to test and calibrate the sensitivity and other parameters of capacitive push buttons (e.g., touch sensitive buttons). Such outputs may also be visualized on a graphical user interface of a computing or testing device to provide visualization of various internal variables and parameters of aspects of the system such as the push buttons.

The contact portion 1606 of the circuit 1600 shows how a voltage source such as a battery is connected. A positive terminal of a battery, J1, serves as VBAT for the circuit 1600. That is, the positive terminal of the battery J1 is connected to pin 4 of the microprocessor 1602 and P1 of the programming portion 1604 of the circuit 1600. The negative terminal of the battery, J2, serves as ground for the circuit 1600. That is, the negative terminal J2 is connected to the second pin of each of the buttons B1, B2, B3, and B4; pins 3, 12, and 21 of the microprocessor 1602; and P4 of the programming portion 1604 of the circuit 1600.

The programming portion 1604 of the circuit may be used to program the microprocessor 1602 to control the LED in different ways. For example, the microprocessor 1602 may be programmed to provide variable user experiences. For example, the microprocessor 1602 may be programmed to change/adjust the brightness of the LED by rotating the finger around the periphery of the outside of a light accessory. This may be accomplished because the touch sensor buttons B1, B2, B3, and B4 may be located along the edge of a circuit board as shown in FIG. 14A, such that movement of a finger around the periphery of the light accessory may be detected. More or less touch sensors may be utilized depending on the size of the light accessory, the size of the touch sensors, the desired sensitivity to movement of a finger, etc., to provide the user experience and variable brightness adjustment desired.

Figure 17:
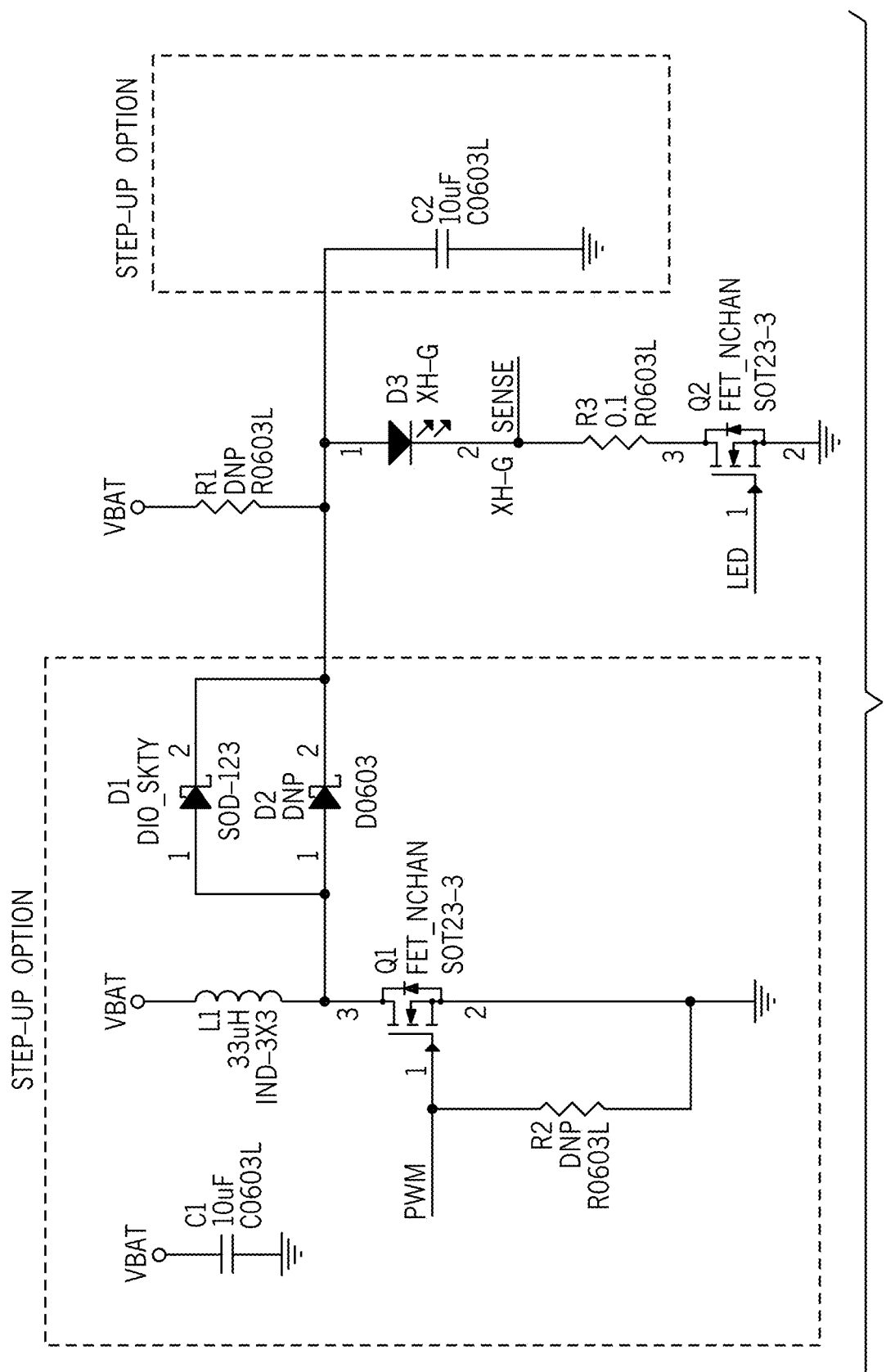
FIG. 17 illustrates a circuit schematic to step up voltage for an example light accessory according to some embodiments of the disclosure.

FIG. 17 illustrates a schematic of a circuit 1700 to step up voltage for an example light accessory according to some embodiments of the disclosure. The circuit 1700 may be used to step up voltage to provide a higher voltage to one or more LEDs than some batteries, such as a lithium primary battery, can provide. In addition, batteries use up their stored chemical energy over time, causing the battery voltage they provide to drop. The circuit 1700 is a step up regulator, controlled by the microprocessor 1602, so that a higher voltage than that provided by the battery may be controlled and supplied to a light source such as an LED. The microprocessor 1602 may control a constant voltage or a constant current via a feedback monitoring and control loop. By controlling the voltage and/or current to the LED, the brightness of an LED may also be controlled in a number of ways. For example, the voltage and or current supplied to the LED may be controlled using a variable drive strength of the microprocessor 1602 I/O pins. For example, pins 1 and 20 (the SENSE line) of the microprocessor may be used in combination with FET Q2 of FIG. 17 to sense the voltage and/or current applied to LED D3 in FIG. 17. The FET Q2 is controlled by a control signal LED from the microprocessor 1602 (connected, for example, to pin 19 of the microprocessor 1602) and a pulse width modulated (PWM) signal (from, for example, pin 2 of the microprocessor 1602) to vary the current and/or voltage applied to the LED D3. When varying the voltage and/or current on the LED D3 via the PWM signal and the step up circuit including L1 and Q1, R3 provides a current sensing signal via pins 1 and 20 using the microprocessor 1602's analog to digital converter. In various embodiments, the circuit 1700 may also be controlled based on the type of LED used. For example, the LED D3 may be of a variety of colors, such as 3000K white, 5000K white, ultra violet, or blue. In various embodiments, multiple different LEDs may be used, and they may be separately controllable using a programmed microprocessor and various touch sensors or other user inputs.

Figure 5:
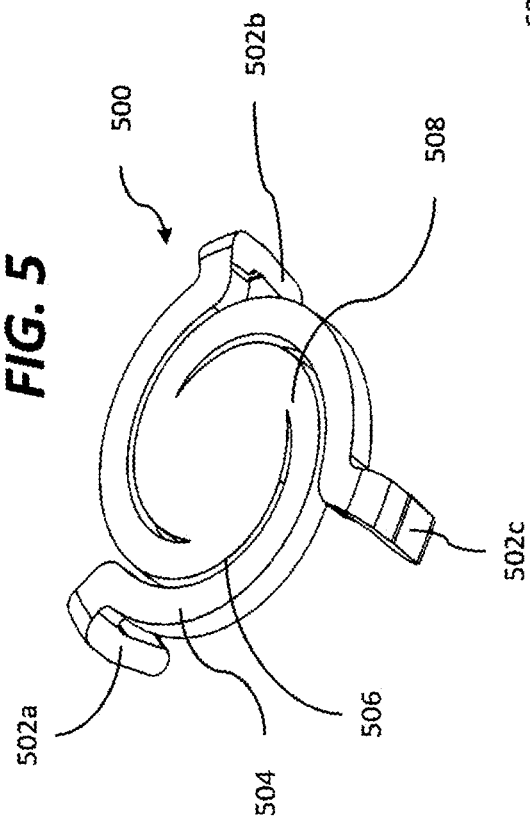
FIG. 5 illustrates a clipping mechanism with flexible legs for an electronic accessory of a stethoscope according to some embodiments of the disclosure.

FIG. 5 illustrates a clipping mechanism 500 with flexible legs 502a, 502b, and 502c for an electronic accessory of a stethoscope according to some embodiments of the disclosure. For example, the clipping mechanism 500 may be attached to the light accessory 400 of FIG. 4, or one of the modules of FIGS. 2 and 3, or some combination thereof. In this way, the clipping mechanism 500 can removably attach a module or accessory to a stethoscope. Similarly, any other clipping mechanism, including the other clipping mechanism examples described herein may be used to removably attach a module or accessory to a stethoscope.

The clipping mechanism 500 includes the three flexible legs 502a, 502b, and 502c that are configured to fit around the bell of a stethoscope. Each of the flexible legs 502a, 502b, and 502c is connected to a main body of the clipping mechanism 500 through an extension from the main body. For example, the flexible leg 502a is connected to the main body through an extension 504 that attaches to the main body at a point 508. A space 506 exists between the extension 504 and the main body. In this way, the flexible leg 502a is even more flexible with respect to the main body so that the clipping mechanism 500 can more easily be attached to and adhere to a stethoscope, as well as stethoscopes of different sizes. The extension 504 extends from the flexible leg 502a, past the flexible leg 502c, and to the point 508 such that a high degree of flexibility may be achieved. A rubberized plastic or other flexible yet sufficiently rigid material may be used for the clipping mechanism 500. Such materials and the shape of the clipping mechanism advantageously allows for greater movement of the flexible legs 502a, 502b, and 502c without damaging the clipping mechanism 500.

Figure 6A:
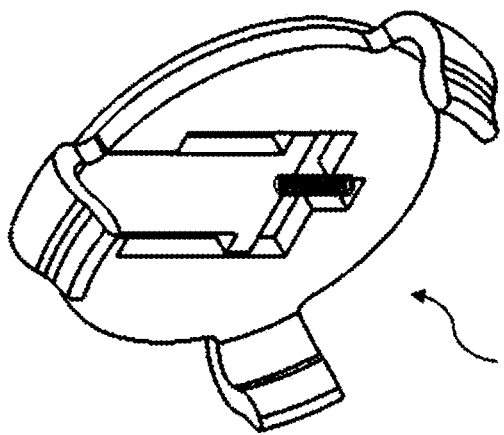
FIGS. 6A and 6B illustrate a clipping mechanism having a spring attached to a leg for an electronic accessory of a stethoscope according to some embodiments of the disclosure.
Figure 6B:
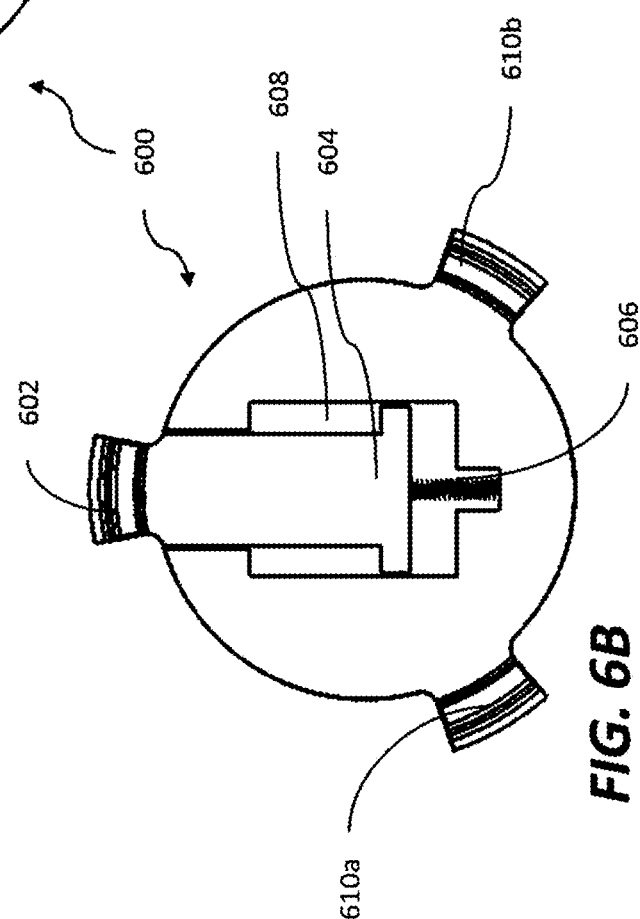

FIGS. 6A and 6B illustrate a clipping mechanism 600 having a spring 606 attached to a leg 602 for an electronic accessory of a stethoscope according to some embodiments of the disclosure. The spring 606 is connected to an extension 604 that is connected to the leg 602. The spring 606 causes the extension 604 and the leg 602 to retract in order to advantageously fit stethoscopes of different bell sizes and shapes to get a universal or semi-universal clipping mechanism. The leg 602 can be pulled away from the main body of the clipping mechanism 600 when it is being attached to a stethoscope, and once it is in place the spring holds the leg 602 onto the stethoscope, further secured by fixed legs 610a and 610b (that is, they are fixed in that they are not movably attached to a spring like the leg 602, but the fixed legs 610a and 610b may still be flexible to some extent). The clipping mechanism 600 may be generally made from rubberized plastic, or may be made from a more rigid plastic since the spring 606 allows for greater range of movement for the leg 602.

FIGS. 7A-7D illustrate a clipping mechanism 700 for an electronic accessory of a stethoscope according to some embodiments of the disclosure. The clipping mechanism 700 has three flexible legs that can clip around a portion of a stethoscope. The clipping mechanism 700 may also be made from a flexible material such as rubberized plastic. The clipping mechanism 700 may also be used to attach a module or accessory to a stethoscope. For example, the clipping mechanism 700 may be used to attach a light accessory (e.g., as described in FIG. 4) to a stethoscope, attach a battery pack to a stethoscope, or to attach any other type of module or accessory to a stethoscope.

FIGS. 8A-8D illustrate a clipping mechanism 800 for an electronic accessory configured to fit different sized stethoscopes according to some embodiments of the disclosure. The clipping mechanism 800 stepped disc can fit in different sized stethoscope bell cavities. The material of the clipping mechanism 800 may have a rubberized/flexible/compressive aspect to it so it can fit multiple sizes of stethoscope bells and fit snugly. In the example of FIGS. 8A-8D, the clipping mechanism 800 has three different stepped discs 802, 804, and 806. In various embodiments, the clipping mechanism

800 may have different numbers of stepped discs, such as two, four, five, etc. The smaller diameter stepped disc portions (e.g., 802, 804) are designed such that for smaller stethoscopes the clipping mechanism 800 will not extend as far into the bell of the stethoscope, offering a greater chance of fit for a greater number of different sized stethoscopes. The clipping mechanism 800 is also hollow within the stepped disc portions, as shown by the space 808 in the cross-section in FIG. 8B. In this way, electronic components (e.g., the light accessory 400 from FIG. 4) may exist inside the space 808, providing a small, sleek package for a modular accessory.

In various embodiments, other clipping mechanisms may be used. For example, some clipping mechanisms may use a surface with adhesive to attach a module/accessory to a stethoscope. Other types of clipping mechanisms may clip a module or accessory onto the hose/tubing, headset, ear pieces, drum, etc. of a stethoscope. For example, a clip may be configured to clip a light accessory, battery accessory, or other module onto the tubing of the stethoscope. Other modules and/or accessories may also be attached to a module/accessory already attached to the stethoscope. For example, a powered I/O connector port may be configured to effectively secure a module/accessory to the stethoscope when it is plugged in to the port.

Another type of module/accessory that may be used with and/or attached to a stethoscope is a percussive device. In various embodiments, a percussive device (or any other module/accessory described herein such as a light, laser vibration detector, etc.) may be used independent of a stethoscope.

Healthcare professionals traditionally have used a diagnostic technique called the percussive technique, using only their hands and senses. The percussive technique is a method of tapping on a surface to determine the underlying structure, and may be used in clinical examinations to assess the condition of the thorax or abdomen. A healthcare professional performing an examination may use such a technique of indirect percussion by placing a spread palm against a surface of the subject, and then tapping the third finger of the hand on the surface of the subject with a third finger of the healthcare professional's second hand. The healthcare professional may then determine what is below the surface (or more generally determine a relative density of what is below the surface) by listening to the response of the tapping. Different sounds indicate different densities of the underlying part of the subject, which may indicate that gas, soft organs, muscle, bone, etc. may be below the surface. There are deficiencies with this long-used method. Significant training, personal experimentation, and recognition of the sounds that only come with experience are useful for the percussive technique to be successful.

A human factor of auditory distinction is a quality factor of the technique. The variation in applied impulse strength (tapping of the finger), duration of the impulse (tapping of the finger), variations in the fingers of healthcare professionals, hearing acuity of healthcare professionals, and more make standardization of percussive methods and results difficult, resulting in ambiguity. While training and experience can mitigate these effects, there is also an inherent healthcare professional distraction leading up to the interpretation phase of the percussion. For example, the healthcare professional concentrates on effecting the percussive impulse, then quickly (e.g., less than a millisecond after) switches concentration to listening to the sound which emanates from the subject's body due to the percussive impulse. This may be difficult for some healthcare professionals.

Further, when practicing indirect percussion, both of the healthcare professional's hands are occupied, leaving it impossible to hold a stethoscope or other tool if desired. (Direct percussive technique may only involve the tapping finger directly onto the surface of a subject, rather than tapping an intermediate finger between the tapping finger and the surface of the subject.) A healthcare professional may also percuss various areas on the body introducing further variability based on how hard the percussive impulse is, etc. In addition, a healthcare professional may repeat the percussive method in the same place because of uncertainty when interpreting results and variability in applying the percussive force.

Accordingly, described herein is a device, method, and computer readable media for implementing a percussive method to enhance the repeatability of delivering a percussive impulse and to aid in interpreting the results by reducing uncertainty and variability.

Figure 9:
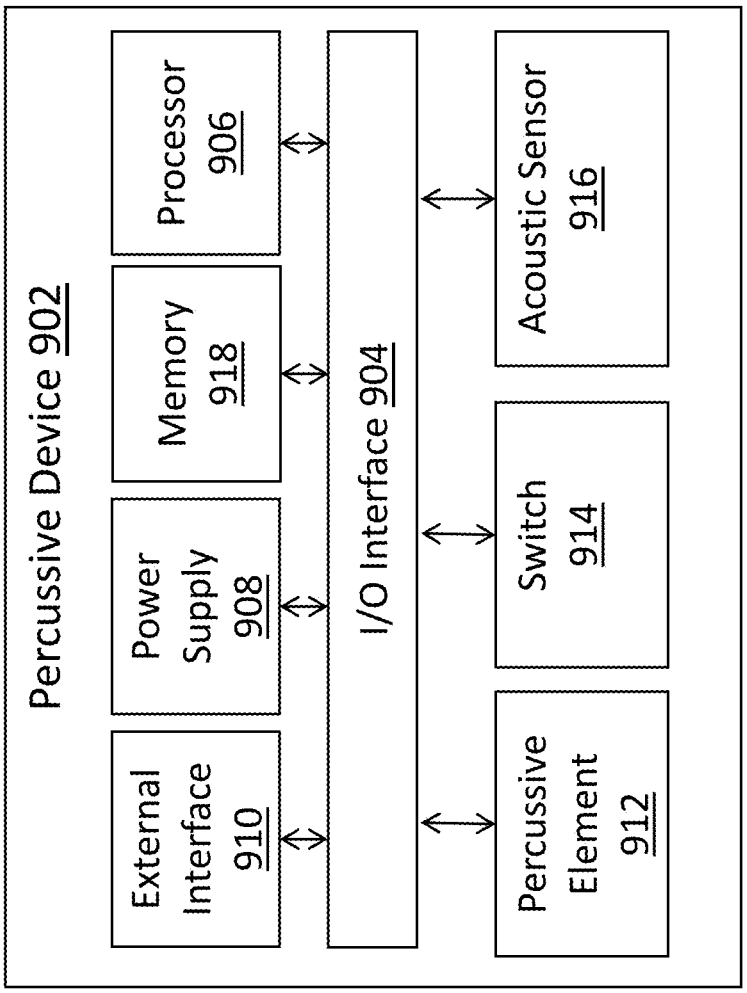
FIG. 9 is a schematic diagram of a percussive device according to some embodiments of the disclosure.

FIG. 9 is a schematic diagram of a percussive device 900 according to some embodiments of the disclosure. The percussive device 900 provides a percussive force to a subject using a percussive element 912. The percussive element 912 may be used to apply a direct or an indirect percussive force, depending on how the percussive element 912 is configured. An example of a percussive element for providing an indirect percussive force is described below with respect to FIG. 10.

The percussive device may further include an I/O interface 904, an external interface 910, a power supply 908, a processor 906, a switch 914, a memory 918, and an acoustic sensor 916. Although shown in a single housing as the percussive device 902, these components may be in separate housings, separable from one another, moveable independent of one another, and/or may be part of another electronic module/accessory. For example, the percussive device 902 may not have its own power supply 908, and instead is supplied by power through the external interface 910 (e.g., through a daisy chained powered I/O as described herein). In another example, the percussive element 912 and/or the acoustic sensor 916 may be movable separate to the rest of the percussive device 902, such that different areas of the body may easily have a percussive force applied or be checked for a response to the percussive force. In various embodiments, rather than having its own acoustic sensor 916, a microphone of another module (e.g., of the electronic stethoscope main units 204 of FIG. 2 or 304 of FIG. 3) may be used as the acoustic sensor to measure a response of the subject to a percussive force.

The switch 914 may be used to turn on and off the percussive device 902. In various embodiments, the switch 914 (or a different switch) may be used to cause the percussive device 902 to deliver the percussive force with the percussive element 912. The processor 906 may be used to control the percussive element 912, analyze signals from the acoustic sensor 916, send information (e.g., signal information received from the acoustic sensor 916) to another computing device through the external interface 910, or for any other function or method as described herein. The memory 918 may have stored thereon non-transitory computer readable instructions that may be executed by the processor 916 to perform any of the functions or methods described herein.

In various embodiments, the percussive device 902 may be removably attachable to a stethoscope. In various embodiments, the percussive device 902 may also be incorporated/integrated into a stethoscope permanently. Whether removably attached to, permanently integrated into, or being used as a standalone device, the percussive device 902 may be advantageously held in and operated using one hand by a healthcare professional. In various embodiments, the percussive device 902 or aspects of the percussive device 902 may be removably attached to a living subject. For example, if the acoustic sensor 916 is outside a main housing of the percussive device 902, the percussive device 902 may be held by one hand while the acoustic sensor 916 is stuck using adhesive to a different location on the living subject. In various embodiments, the percussive device 902, the percussive element 912, etc. may also be adhered to the living subject. The percussive device 902 may also be used as a module in conjunction with other modules/accessories described herein (regardless of whether the percussive device 902 is used with a stethoscope). As just some examples, a battery module may be used to power the percussive device, microphone and/or signal processing modules may be used in conjunction with the percussive device 902 to pick up and process the acoustic response of the subject to the percussive force, etc.

In various embodiments, having an extra free hand may allow a healthcare provider to hold the drum/bell end of a stethoscope to listen with stethoscope with their free hand. In such an embodiment, the acoustic sensor (e.g., microphone) of an electronic stethoscope may be used in addition to or instead of the acoustic sensor 916 to detect a subject's response to the percussive force. Where the percussive device 902 is adhered to or otherwise attached to the subject, the use of the device may be hands free for the healthcare professional.

Advantageously, an electronic application of a percussive force allows a healthcare professional to focus on the output of the subject (e.g., their response to the percussive force) rather than applying the percussive force. The embodiments described herein also advantageously apply more predictable and certain percussive forces, leading to more meaningful outputs/responses. In addition, the embodiments herein provide for applying a percussive force that has qualities that are consistent, metered (measurable and quantifiable), and repeatable. The embodiments herein also provide for a healthcare professional to adjust the percussive force as desired, and the amount or magnitude of that force may be indicated via a metered force dial that the healthcare professional may adjust and/or some sort of analog or digital display feedback to indicate the magnitude of the percussive force being applied.

Further, the sound of a response of a subject to a percussive impulse may also be recorded by the percussive device 902 and stored in the memory 918 (or may be recorded/stored by a device the percussive device 902 is in communication with). This may provide benefits such as transmitting the response to other devices, including for example remote healthcare providers. The responses may also be used for teaching, and may be stored as part of a health record to be referred to later. For example, a healthcare professional may wish to listen to a subject's historical response to a percussive impulse in addition to listening to their current response to a similar percussive impulse to gauge for changes in the density/makeup of a particular portion of the subject. In another example, a healthcare professional may also replay the results that have just been recorded to gain clarity on what was heard. This may all advantageously further improve the accuracy and meaningfulness of the percussive technique.

Audio processing may also be performed on a captured response to slow down a captured audio waveform. In various embodiments, processing that preserves pitch/frequency may also be used. Such processing may help the observer's audio senses have extended time to interpret the audio response of the subject to the percussive impulse. A captured waveform may also be displayed on an x/y graph wave form display or any other type of display. This may allow an observer to see responses/echoes visually. The location of where the percussive force is applied and/or the location of the listening/sensing device may be changed/adjusted to enhance resolution and/or meaning of the results of the percussive method as described herein.

Various other processing may also be advantageously performed on the captured audio signal. For example, processing may be done to automatically identify echoes and determine metrics such as time and or intensity characteristics of those echoes.

An impulse (such as that applied by the percussive device 902) may be theoretically characterized as an imaginary signal with all frequencies. If such an impulse is fed into a filter, then the aspects/characteristics of that filter may be characterized by reading the impulse response. Similarly, the percussive impulse is the introduction of many frequencies into the body of a subject as energy. The sound of the response to that impulse may similarly characterize aspects of the subject. In other words, the returning sound may include intensity fronts, indicating characteristics of what is inside the subject.

With such a concept in mind, an enhanced percussive device may have multiple acoustic sensors that may be placed at different locations on the subject's body. In other words, a percussive device may deliver a percussive force at a single location and have a number N listening devices at locations around the body. The response waveform sensed at each acoustic sensor is digitized. The time correlation may be synced among them, and the relative positions of each acoustic sensor on the body may be noted and preserved (and associated electronically with the waveforms captured). With this information, a three-dimensional (3D) map of the acoustic density of the body may be created. The granularity and resolution of the 3D map may be a function of the number N and any processing that is done to those waveforms. This offers many improvements and advantages over traditional percussive technique interpretation.

Figure 10:
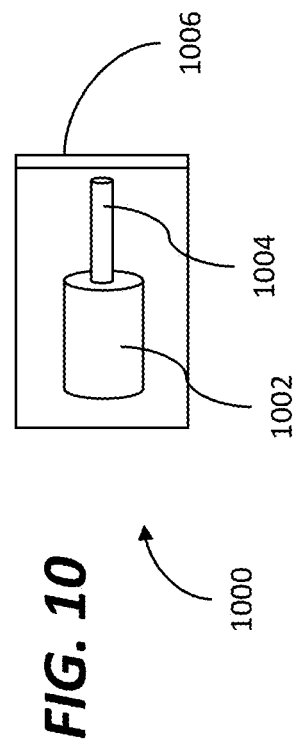
FIG. 10 is a schematic diagram of a percussive element of a percussive device according to some embodiments of the disclosure.

FIG. 10 is a schematic diagram of a percussive element 1000 of a percussive device according to some embodiments of the disclosure. The percussive element 100 includes a linear actuator 1002. The linear actuator 1002 is configured to move a plunger 1004 linearly in response to application or removal of an electrical signal. The percussive element 1000 also includes a membrane 1006 having a first surface and a second surface. The first surface is opposite the second surface. The linear actuator 1002 moves the plunger 1004 in response to an electrical signal such that the plunger 1004 impacts the first surface of the membrane, providing an indirect percussive force through the membrane 1006 to a surface of a subject on the second surface of the membrane 1006. The membrane 1006 is configured to transmit that percussive force from the first surface to the second surface as a result of the plunger 1004 impacting the first surface of the membrane 1006. In various embodiments, the percussive device 1000 may not have the membrane 1006, and therefore may apply a direct percussive force to a subject. In various embodiments, the plunger may also have a coating, such as a coating with a similar acoustic density to human skin and/or fat tissue (or some combination thereof), or any other type of specialized coating. In other embodiments, the plunger may not have a particular coating.

In various embodiments, the linear actuator 1002 is an electromechanical solenoid. In various embodiments, any other type of inertial element that is electromotive driven to provide an impact force may be used instead of a linear actuator. For example, a voice coil may also be used. Voice coils may be highly controllable, allowing for consistent and dependable impact. In various embodiments, a release of stored energy may also be used to apply a percussive force. For example, energy may be stored in a spring that is compressed, and that energy may be released via mechanical and/or electromechanical components as desired by the user and/or the control circuitry of the electronic stethoscope. Accordingly, various types of electromechanical or electromagnetic solenoids may be used as the linear actuator 1002.

The percussive element 1000 may also include a housing designed to be held in one hand or to be strapped or otherwise adhered to the patient, or may be combined into a housing of the percussive device 902 as described herein. Accordingly, the percussive element 1000 mimics the finger tapping percussion technique for detecting tissue density based on sound.

Figure 11:
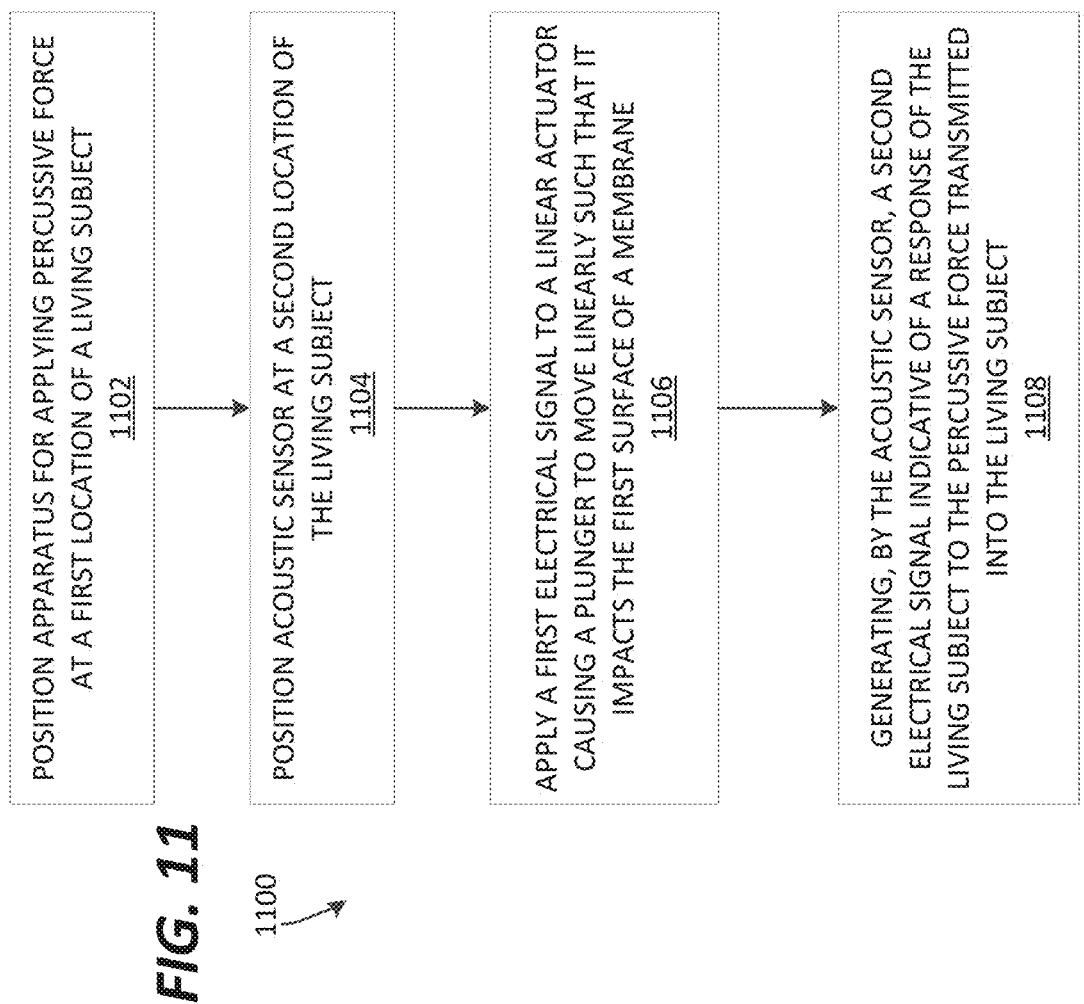
FIG. 11 is a flow diagram illustrating a method for using a percussive device according to some embodiments of the disclosure.

The plunger 1004 and/or the membrane 1006 may be made of materials of similar acoustic density to human bone to more closely simulate manual percussive technique. In other words, the membrane and/or the plunger 1004 may have an acoustic density within the range of the average acoustic density of human bone. For example, an elastomer with an acoustic density similar to human skin and/or fat tissue (or some combination thereof) may be used, which is put in contact with the subject's skin to provide an interface for the percussive device with the subject. In another example, the membrane 1006 may be made of a hard plastic with a rubber coating or layer on the outside to approximate a finger with a rigid inside and a softer outside. The plunger 1004 may also be rigid with a rubber coating or layer to again approximate a finger. As described herein, the percussive element 1000 may apply a percussive force at a consistent, repeatable power and interval. The percussive element 1000 may also apply variable levels of percussive force and/or percussive momentum. The percussive element 1000 may be mounted on a stethoscope, such as on a head of a stethoscope. The percussive element 1000 may also be a separate device from a stethoscope. A stethoscope, such as those described herein whether acoustic or electronic, may be used to detect a signal that passes through the body of a subject as a result of a percussive force applied by the percussive element 1000. If an electronic stethoscope is used, various signal processing techniques may be utilized to recognize patterns or characteristics of the signal detected. For example, the signal processing may determine if the signal has passed through liquid, gas, bone, etc., such that an electronic stethoscope may be used to automatically determine and notify a user of a change or abnormality FIG. 11 is a flow diagram illustrating a method 1100 for using a percussive device according to some embodiments of the disclosure. The method 1100 may be implemented using a percussive device as described herein, such as the percussive device 902 of FIG. 9.

At operation 1102, an apparatus for applying a percussive force is positioned at a first location of a living subject. At an operation 1104, an acoustic sensor is positioned at a second location of the living subject. Operations 1102 and 1104 may be distinct if the apparatus for applying a percussive force and the acoustic sensor are movable separate from one another. In various embodiments where the apparatus for applying the percussive force and the acoustic sensor are not movable separate from one another, the operations 1102 and 1104 may be performed simultaneously.

At an operation 1106, a first electrical signal is applied to a linear actuator causing a plunger to move linearly such that it impacts a first surface of a membrane. As described herein, the membrane may include a second surface opposite the first surface, and the membrane transmits a percussive force from the first surface to the second surface and into the living subject as a result of the plunger impacting the first surface of the membrane. As also described herein, the first electrical signal may be controlled to cause a desired magnitude, length, momentum, etc. of the percussive force delivered by the linear actuator.

At an operation 1108, a second electrical signal indicative of a response of the living subject to the plunger impacting the membrane and transmitting the percussive force into the living subject is generated by the acoustic sensor. A signal captured by the acoustic sensor may be translated into data indicative of the second electrical signal. That data may be saved to a memory of a computing device. That saved data may be used to play the second electrical signal through a speaker at a time after the second electrical signal was generated. A visualization indicative of the second electrical signal may also be displayed on a display of a computing device as described herein.

That visualization of the second electrical signal may be considered a first visualization. Subsequent percussive method tests may be performed on the same subject at the same or different locations on the body at the same or at different times, or may be performed on different subjects at the same or different locations on the body at the same or at different times. Visualizations from those percussive instances may be compared to the first visualization on a display.

Similarly, other acoustic sensors may be placed on the subject to capture data on responses of the same subject in different locations to the same percussive force. Those responses may also be visualized and compared to other responses. All of these visualizations and data may be further analyzed to study for patterns with respect to an individual, a population or demographic, over time, etc.

Other various signal processing techniques may be used in conjunction with the detected signals described herein. For example, signals may be detected and processed when using a percussive element as described herein to shift inaudible frequencies into frequencies that are audible to humans. In this way, insights may be achieved that were previously not possible using a percussive technique. Various processing to provide signal equalization may also be used. For example, processing may make higher frequencies a higher volume (e.g., increase amplitude) and lower frequency lower volume (e.g., decrease amplitude) so a user can hear a wide band of frequencies appropriately without losing information. In addition, certain frequencies could be isolated so that a user only hears certain frequencies that may be indicative of certain information, or may be easier to interpret if other frequencies are filtered out. Users may also customize the frequencies they would like to hear or the volume the prefer for different frequencies into different predetermined audio settings.

The various systems and methods described herein may also use algorithms to study data from signals captured to look for patterns over time in the data/signals. For example, machine learning may be used to train a model/algorithm for recognizing patterns in data/signals. For example, once a model/algorithm is trained to identify patterns or indicators of certain health problems, conditions, or risk factors, signals captured at different times of the same patient may be fed into the algorithm to detect changes or indicators of particular issues.

The various systems and methods described herein may also provide telemedicine uses and applications. For example, in real time, data/signals captured may be visualized for a telemedicine health provider remotely. A telemedicine health provider may also be able to remotely hear audio signals captured and processed. Analysis of the data/signals may also be automated in real time, which may be viewed and/or interpreted by the telemedicine provider. The repeatability of force possible using the percussive device provided herein provides useful input data to get reliable and helpful output audio/signals from a patient. Accordingly, the output signals/data related to multiple time correlated percussions may be blended, compared, etc. in ways that would not be reliable using a hand/finger percussive method because the input percussive force could not be replicated and controlled. The repeatability also provides the ability to apply the same amount of force in slightly different locations on a patient, further enhancing the usefulness of data/signals detected from one or more locations on a patient.

Signal processing may also include windowing a detected percussive response. For example, a percussive device as described herein may be used to introduce energy into a person's body for the purpose of diagnosing what is inside the body. One problem with using a traditional acoustic stethoscope with the percussive method is that a large initial sound, which is directly caused by the percussion, is loud compared with the diagnostic portion which comes in a short amount of time, directly after the initial, direct percussive response. Human physiology is such that the initial direct response may be very loud and/or unpleasant to a listener if the following, fainter sound response is to be heard. In other words, because the fainter response is so close in time to the initial direct response, there is little to no time to manually adjust a volume perceived by the user by, for example, keeping an acoustic stethoscope away from the subject during the louder direct response and then moving the stethoscope into contact with the subject for the fainter, diagnostically important response. In addition, a loud sound, even if unpleasant, followed by a faint sound may cause the perception of the faint sound to be diminished.

However, using an electronic stethoscope and signal processing may alleviate or solve these issues. For example, the amplitude of the fainter sound may be increased following the initial percussive event, which will aid in perception of the healthcare provider. Signal processing may be used to correlating a time windowed attenuation or elimination of the initial direct percussion sound. That is, the initial louder sound may be identified and have its amplitude reduced or event eliminated so that it is not heard by the user. The more important auditory data may then be concentrated on by a user without perception distraction caused by the louder signal. The fainter, diagnostically important signal may also have its frequency shifted to a spectrum of hearing which most people have better auditory recognition (e.g., the frequency band in which human speech occurs). The isolated diagnostically important signal may also be slowed down (e.g., stretched in time) while keeping the frequency content intact with the option to also shift the frequency as mentioned herein to a range better suited for a human listener.

Sampling, recording, and/or visualization of the faint response may also be performed. The sampling, recording, and/or visualization may be done before or after various aspects of signal processing described herein. In this way, a raw signal and/or a processed signal may be saved. Where a raw signal is saved, this may be valuable as various signal processing may be applied to the raw signal later in time to determine different information, test the efficacy of different signal filtering, etc. Accordingly, various filtering, replay (e.g., one percussion performed but many chances to listen), frequency equalization, etc. may all be utilized. Visualization of a signal, such as graphing the faint waveform on a phone or other display with time or distance estimation markers may also be used to show, for example, impulse response echoes. A thresholding algorithm may also be used to determine known or sampled heuristics to guide clinician to a diagnostic conclusion based on the captured signal. Remote diagnostics of the contents of internal cavities may also be performed using a saved signal. Patient administered percussion may also be possible, and the signal may be interpreted remotely or at a later time, by a healthcare provider and/or with an automated process. Data/signal responses to multiple time correlated percussions may also be blended to get an average response, compared to determine changes over time, etc. Blended signals may also provide data with reduced signal to noise ratio or other errors.

The various percussive methods described herein may also be used on other bodies than human bodies. For example, the device may be used on rocks to determine if they are hollow, such as with certain types of geodes.

FIG. 12 is a schematic diagram of a laser detection device 1200 for measuring vibrations of a surface of a living subject 1206 according to some embodiments of the disclosure. The laser detection device 1200 includes a laser emitter 1204, which emits a first laser beam 1212 and a second laser beam 1216. The first laser beam 1212 reflects off of the living subject 1206 at a point 1210. The first laser beam 1212 interacts with the living subject 1206 at the point 1210, and at least some of the light from the first laser beam 1212 reflects off of the living subject 1206 as a first reflected laser beam 1214. Although the first return/reflected laser beam 1214 includes some of the same light as the first laser beam 1212, it is not all of the light from the first laser beam 1212 and the light of the first reflected laser beam 1214 may have different characteristics of the first laser beam 1212. Accordingly, for clarity, the emitted laser beam from the emitter 1204 and the beam that results from reflection off the living subject 1206 are referred to herein as separate beams: the first laser beam 1212 and the first reflected laser beam 1214. Similarly, the emitter 1204 also emits a second laser beam 1216 that reflects off the living subject 1206 at a point 1208, resulting in second reflected laser beam 1218. In an alternative embodiment, the laser emitter 1204 only emits a single laser at a time, and the beams 1212 and 1216 shown in FIG. 12 are emitted at different times to reflect off of two different locations of the living. In any embodiment, the practical effect is the same, that vibrations at multiple points on the surface of a living subject may be detected, whether at the same time or at different points in time. In particular, changes in amplitude from an emitted beam after it has been reflected are measured to detect vibrations on the surface of the living subject.

The first reflected laser beam 1214 and the second reflected laser beam 1218 may be detected by a detector 1202. Changes in the beams 1214 and 1218 detected by the detector may be used in conjunction with what is known about the emitted beams 1212 and 1216 to determine aspects of the surface of the living subject 1206 at the points 1208 and 1210, such as vibrations. Vibrations may be indicative of breathing, blood flow, etc. Such methods and systems may be valuable for checking vitals such as breathing and pulse from long range. The output from the detector could also be processed and sent to a speaker or headphones so that someone can hear the vibrations of the living subject from afar.

This enhanced system for detecting vibrations of the surface of a living subject has several advantages. The acoustic stethoscope is large and heavy, relative to the embodiments of a laser detection device described herein. The acoustic stethoscope also uses intimate surface contact with the skin of a subject, which may be avoided using the laser detection device. Further, movement of the stethoscope on the surface creates a noise which corrupts a received signal. Advantageously, this does not occur with the laser detection device described herein.

The laser beams 1212 and 1216 emitted by the emitter 1204 may have similar or different characteristics. For example, the characteristics may be varied based on what is being measured and/or a location of the body the beams are pointed at. The varied characteristics may be frequency, phase, amplitude, color, whether the laser is visible to humans or not, or any other aspect.

The laser beam(s) may be pointed to a location on the body where a healthcare professional or other operator knows there is a good potential to pick up vascular surface vibrations or the sounds created when a person breathes. Surface vibration cause the reflected laser beam to vibrate in terms of the reflection intensity at a given direction. These surface vibrations are representative of the sounds from inside the body.

The laser frequency (wavelength) of the emitted beams may, in various embodiments, be visible or invisible (e.g., infrared, ultraviolet). A visible spot laser may also be added to accompany an invisible laser. This is to allow an operator to know where the laser emitter is pointed, i.e. where the invisible laser spot is on the body. This may include a way to switch off the visible laser after the location the invisible laser is pointed at is known. In other words, a visible laser beam is used to illuminate a point of the surface of the living subject at which an invisible laser beam is directed.

The laser beam direction and receiver direction are such that the optics of the receiver are looking in the direction of the laser point emitted by the emitter. However, the field of view of the receiver and the size of the laser beam spot may be expanded or configured as desired.

In various embodiments, emitted beams may be modulated to a high frequency, such as 500 kilohertz (KHz), 1 megahertz (MHz), 10 MHz, or another frequency. The modulation is such that the laser light intensity has a frequency component of a known value or inside a known frequency range. Other frequency harmonics and direct current (DC) may exist in the modulated laser energy spectrum, but may be removed from a detected beam so that the actual vibrations of the surface of the living subject may be determined. For example, an emitted beam is modulated to a high frequency and aimed toward a living subject. The beam then reflects off the living subject and is picked up by a detector. That detected reflected beam is then demodulated to remove the carrier frequency and isolate the aspects of the reflected beam related to the vibrations of the surface of the living subject. In order to demodulate the reflected beam, a detector may include components to detect both an optical field of view and laser light frequencies. For example, the detector may include one or more laser light frequency filters. In this way, the detector can use the optical field of view and laser light frequency detection components to discriminate between and isolate the surface modulated signal (the reflected laser beam) from any unwanted signals (e.g., ambient light in the room, movement of patient, etc.). In just one example, the detector may be focused and/or zoomed in on the location of the reflected laser beam, and a notch color/infrared (IR) pass filter preceding the detector to help isolate the light of interest (the reflected laser beam).

The detector receives the high frequency modulated laser light, whose received energy intensity has been further modulated by the movement of the surface of the body. The vibration information of the body surface is present in the high frequency as a superimposed image of the surface vibration in the frequency domain, centered around the high frequency signal. Demodulation techniques may be used to extract the surface vibrations from the high frequency signal. For example, amplitude modulation (AM) may be used to modulate and demodulate beams/signals. In various embodiments, a standard AM receiver may be used to demodulate the skin surface vibration information contained in the high frequency received signal and convert them to a base band signal. The base band signal may be listened to in real time by an operator and/or recorded/stored. Such modulation reduces ambient noise and ambient light interference. In addition, the unintended movement of the laser beam over the skin may otherwise create distortion in the signal.

The target location of the laser beam spot may be moved by several means. The purpose is to allow for listening and mapping of the vibrations related to the heart and or vascular vibrations. The mapping may be a simple manual mode where the operator manually changes the spot position and observes and or records the resulting vibrations.

In an enhanced device, the manual movement may be tracked by the means of inertial, rotational and gyroscopic sensors present in the device. This provides a correlation between the set of vibration measurements and the relative position on the subject's body. A further enhancement is the means of providing a start point input means. The start point may be any pre-defined point on the body and requires operator to provide an input to the system that the laser spot is on a particular point of the body. Other body metrics can be used such as shirt size, height, weight, body width to further enhance the positional knowledge of the system.

An automated scanning method may also be implemented with a laser detection device (e.g., the laser detection device 1200 of FIG. 12). Such a scanning method, through mechanically controlled motion of the emitted laser beam(s), including position and rotation of the laser emitter (and detector accordingly) may scan sections of the body, correlating the vibrations detected to the position of the body of the body currently being scanned. The operator or system may either start the scan at a predefined position or record the start position. Similarly, the end of the scan may be predefined or manually implemented by an operator. Information about a subject's body may also be noted using an automated process, so that the region of the body scanned is noted, and the system may determine a starting or ending position based on information about a particular body. This may be done to better define body position of the variable position laser spot and note exactly the part of each body scanned.

In various embodiments, mirrors may be rotated in front of the laser beam and detector optical path for the purpose of moving the laser spot and correlation of the location monitored and or recorded on the body. In this way, instead of mechanically moving the detector and/or emitter, only the mirrors are moved.

Various embodiments may have a fixed, omnidirectional detector. Such embodiments may have several advantages. For example, the receiver may not use as much battery power (e.g., the field of view of the receiver/detector does not need to be as large). In such embodiments, battery power may be used on more processing and amplification of the emitted and detected signals.

Various embodiments may also have recording, wide area network (WAN) connection capabilities through which the devices may communicate information captured and/or be controlled. Storage/memory and/or other signal processing and communication aspects may also be implemented.

As described herein, various modules may be used for an operator or some other person to listen to the surface vibration detected by a laser detection device. Such vibrations may have been converted to an audio signal via speaker, headphone, communicated via wireless to a phone, wireless speaker, remote listening device, etc. In other words, the laser detection device may be used in conjunction with other modules/accessories described herein, such as the speaker and/or headphone modules described above with respect to FIGS. 2 and 3. Other modules may also be used with a laser detection device, such as a battery module, signal processing module, etc. Although the laser detection device may be used instead of a stethoscope, the laser detection device may still be attachable to a stethoscope or may be used independent of a stethoscope. In various embodiments, the laser detection device may be substitute for the stethoscope in any of the embodiments described herein, such that any of the modules/accessories described herein may interact with and/or be used with the laser detection device. In such examples, the laser detection device outputs a signal that may be used, processed, visualized, etc. similar to a signal picked up by a microphone or other sensor of electronic stethoscope or electronic stethoscope module as described herein. Prior to or after transmission or conversion of such a signal, the signal from the surface of the skin, which represents faithfully the movement at a small spot area, may be enhanced by one or more signal processing components and/or modules. One such enhancement could be to filter the true signal such that it sounds like the false or distorted signal clinicians are familiar hearing from the common stethoscope due to noise. Other adjustments and processing such as amplitude adjustments and others are described herein.

The signal captured by a laser detection device may also be digitized. This digital form may have many advantages. The digitized skin vibrations may be accompanied by/stored with position information of where on the body the vibration data was collected. A matrix or a myriad of data may be captured and created. The data may be listened to remotely by transmitting the data, then converting the base band vibration data to sound as described herein. Such uses may be valuable in telemedicine.

In addition, the digital data may be amplified, waveform shaped, enhanced, filtered, etc. using audio processing techniques. For example, digital signal processing algorithms for noise reduction, equalizing, amplification, automatic gain control, and any other processing may be used. Such processing may be performed locally in the laser detection device, on a separate hand-held device, in the cloud, on another computing device, and/or raw data may be stored for later review and processing.

The separate locations scanned may be combined and looked at (visualized on a display) or listened to as a set. Accordingly, individual data sets taken at different locations may be synchronized and/or combined. This may also advantageously remove time variations and other disparate artifacts. Various embodiments may also have two or more detection devices operating simultaneously. This provides for capturing of data at the same time of two locations (e.g., at two locations in a blood flow path).

FIG. 13 is a flow diagram illustrating a method 1300 for measuring vibrations of a surface of a living subject according to some embodiments of the disclosure. At an operation 1302, a first laser beam is emitted and directed at the surface of the living subject. The first laser beam is configured to interact with the surface of the living subject such that a reflected laser beam reflects from the surface of the living subject. The reflected laser beam has different characteristics from the first laser beam at least in part due to the interaction with the surface of the living subject and the vibrations of that surface.

At an operation 1304, the reflected laser beam that is reflected from the surface of the living subject is detected. At an operation 1306, the detected reflected laser beam is processed to determine vibrations of the surface of the living subject. The output after processing may be a signal that may be output as audio and approximates a sound of the vibrations of the surface of the living subject that would be detected if a stethoscope was used to detect the vibrations. The processing may also filter out ambient noise and light interference. The system may also output, after the processing, a visualization indicative of the vibrations to a display of a computing device.

Various signal processing may also be used along with the remote sensor/laser device and methods described in FIGS. 12 and 13. For example, amplitude or frequency modulation of the output signal of the device may be used, so that when a response signal is detected, the response signal may be demodulated to determine the data of interest. This may assist in accurately determining data embedded in a signal and protect the data against corruption from noise, a weak signal, etc., providing higher sensitivity and accuracy of the device.

In various embodiments, microwave signals (e.g., a 24 GHz radar) may be used to detect movement of a subject to monitor, for example, breathing and/or heart rate. Such a device may be incorporated into a modular stethoscope as described herein. An accelerometer may also be incorporated into a modular stethoscope or otherwise be worn by a subject, so that if the subject (e.g., heart, chest, etc. of a subject) moves that movement may be accounted for.

Other devices may also be incorporated into a modular stethoscope as described herein. For example, an $SPO_2$ sensor or an electrocardiogram (EKG or ECG) device may also be incorporated into a modular stethoscope as either removable or permanent components.

Various embodiments are further described in the numbered clauses below:

Clause 1. An electronic stethoscope apparatus comprising:
  a microphone configured to generate an electrical signal in response to received sound from a living subject;
  amplification circuitry operably coupled to the microphone and configured to amplify the electric signal generated by the microphone;
  a speaker operably coupled to the amplification circuitry and configured to output the electric signal after amplification; and
  a power supply configured to power the amplification circuitry.

Clause 2. The electronic stethoscope apparatus of clause 1, wherein the microphone is embedded into tubing connected between a diaphragm and an ear piece, wherein the tubing is configured to allow acoustic sound waves to travel from the diaphragm to the ear piece, and wherein the microphone does not impede the acoustic sound waves from traveling within the tubing.

Clause 3. The electronic stethoscope apparatus of clause 1, further comprising a power output port operably coupled to the power supply and configured to provide power from the power supply to a modular electronic device configured to removably connect to the power output port.

Clause 4. The electronic stethoscope apparatus of clause 1, further comprising a processor configured to determine whether the electronic stethoscope is in use, and wherein the processor is further configured to:
cause power to be provided to the amplification circuitry while the electronic stethoscope is in use; and
cause power to not be provided to the amplification circuitry while the electronic stethoscope is not in use.

Clause 5. The electronic stethoscope apparatus of clause 4, wherein the determination that the electronic stethoscope is not in use is made based on whether a headphone is plugged into a headphone port on the electronic stethoscope.

Clause 6. The electronic stethoscope apparatus of clause 4, wherein the determination that the electronic stethoscope is not in use is made based on whether a wireless headphone is wirelessly connected to the electronic stethoscope.

Clause 7. The electronic stethoscope apparatus of clause 4, wherein the determination that the electronic stethoscope is not in use is made based on an amplitude of the electrical signal generated by the microphone is below a predetermined threshold.

Clause 8. The electronic stethoscope apparatus of clause 4, further comprising a motion sensor, and further wherein the determination that the electronic stethoscope is not in use is made based on an output of the motion sensor.

Clause 9. The electronic stethoscope apparatus of clause 8, wherein the output of the motion sensor indicates that the electronic stethoscope has not been moved for at least a predetermined threshold of time.

Clause 10. A light apparatus comprising:
a light;
a switch to turn the light on or off; and
a clipping mechanism configured to attach the light apparatus to a bell portion of a stethoscope, wherein the switch is accessible while the light apparatus is attached to the bell portion.

Clause 11. The light apparatus of clause 10, wherein the clipping mechanism comprises flexible, rubberized plastic configured to deflect when attaching the light apparatus to the stethoscope or detaching the light apparatus from the stethoscope.

Clause 12. The light apparatus of clause 11, wherein the flexible, rubberized plastic is configured to dampen noise from passing from the light apparatus into the stethoscope.

Clause 13. The light apparatus of clause 10, wherein the clipping mechanism is configured to fit on at least two different sized bells of at least two different stethoscopes.

Clause 14. The light apparatus of clause 10, wherein the light apparatus is configured not to block any portion of a diaphragm of the stethoscope when the light apparatus is attached to the bell portion of the stethoscope.

Clause 15. The light apparatus of clause 10, wherein the clipping mechanism comprises at least two arms configured to wrap around the outer perimeter of the bell portion.

Clause 16. The light apparatus of clause 15, wherein at least one arm of the at least two arms is operably connected to a spring, such that the at least one arm is movable when attaching the light apparatus to the bell portion and the spring holds the at least one arm in place after the light apparatus is attached to the bell portion.

Clause 17. The light apparatus of clause 10, wherein the light is powerable by a battery and the battery is at least one of:
stored directly in the light apparatus; or
stored in a different portion of the stethoscope than the light apparatus and wherein the light apparatus is electrically connected to the different portion through an electrical wire.

Clause 18. The light apparatus of clause 17, wherein the battery is stored in the different portion of the stethoscope, and the electrical wire is removably connected to the light apparatus.

Clause 19. The light apparatus of clause 17, wherein the battery is stored directly in the light apparatus, and the light apparatus further comprises a port for removably connecting a device to the light apparatus, such that the device is powered by the battery.

Clause 20. The light apparatus of clause 17, wherein the battery is stored directly in the light apparatus and the battery is configured to be at least one of:
removable from the light apparatus such that the battery is changeable when the battery dies;
non-removable from the light apparatus; or
rechargeable.

Clause 21. An apparatus for applying a percussive force to a living subject, the apparatus comprising:
a membrane having a first surface and a second surface, wherein the first surface is opposite the second surface; and
a linear actuator configured to move a plunger linearly in response to application or removal of an electrical signal, wherein:
the linear actuator is configured to move the plunger such that the plunger impacts the first surface of the membrane; and
the membrane is configured to transmit a percussive force from the first surface to the second surface as a result of the plunger impacting the first surface of the membrane.

Clause 22. The apparatus of clause 21, wherein the linear actuator comprises an electromechanical solenoid or a voice coil.

Clause 23. The apparatus of clause 21, wherein the linear actuator is actuated by an energy storage device.

Clause 24. The apparatus of clause 21, wherein the apparatus is configured to be removably attachable to a stethoscope.

Clause 25. The apparatus of clause 21, wherein the apparatus is incorporated into a stethoscope.

Clause 26. The apparatus of clause 21, wherein the membrane has an acoustic density within the range of the average acoustic density of human bone.

Clause 27. The apparatus of clause 21, wherein the apparatus is configured to be held in one hand.

Clause 28. The apparatus of clause 21, wherein the apparatus is configured to be removably attached to the living subject.

Clause 29. A method comprising:
positioning an apparatus for applying a percussive force at a first location of a living subject;
positioning an acoustic sensor at a second location of the living subject;

applying a first electrical signal to a linear actuator causing a plunger to move linearly such that it impacts a first surface of a membrane, wherein:
the membrane comprises a second surface opposite the first surface, and
the membrane transmits a percussive force from the first surface to the second surface and into the living subject as a result of the plunger impacting the first surface of the membrane; and generating, by the acoustic sensor, a second electrical signal indicative of a response of the living subject to the plunger impacting the membrane and transmitting the percussive force into the living subject.

Clause 30. The method of clause 29, wherein the first electrical signal is controlled to cause a desired magnitude of the percussive force.

Clause 31. The method of clause 29, wherein the first electrical signal is controlled to cause a desired length of the percussive force.

Clause 32. The method of clause 29, wherein the membrane has an acoustic density within the range of the average acoustic density of human bone.

Clause 33. The method of clause 29, wherein the linear actuator comprises an electromechanical solenoid or a voice coil.

Clause 34. The method of clause 29, wherein data indicative of the second electrical signal is saved to a memory of a computing device.

Clause 35. The method of clause 34, further comprising playing the second electrical signal through a speaker using the saved data at a time after the second electrical signal was generated.

Clause 36. The method of clause 29, wherein a visualization indicative of the second electrical signal is displayed on a display of a computing device.

Clause 37. The method of clause 36, wherein the visualization of the second electrical signal is a first visualization, the response of the living subject to the plunger impacting the membrane and transmitting the percussive force into the living subject is a first response, and further wherein:
the second electrical signal was captured at a first time;
a second visualization is displayed on the display along with the first visualization;
the second visualization is indicative of a third electrical signal;
the third electrical signal is indicative of a second response of the living subject to the plunger impacting the membrane and transmitting the percussive force into the living subject; and
the third electrical signal is captured at a second time different from the first time.

Clause 38. The method of clause 29, wherein the acoustic sensor is a first acoustic sensor, and further comprising:
positioning a second acoustic sensor at a third location of the living subject, the third location being different than the second location; and
generating, by the second acoustic sensor, a third electrical signal indicative of the response of the living subject to the plunger impacting the membrane and transmitting the percussive force into the living subject.

Clause 39. An apparatus for measuring vibrations of a surface of a living subject, the apparatus comprising:
an emitter configured to emit a laser beam directed at the surface of the living subject, wherein the laser beam is configured to interact with the surface of the living subject such that a reflected laser beam reflects from the surface of the living subject, and further wherein the reflected laser beam has different characteristics from the laser beam at least in part due to the interaction with the surface of the living subject;
a detector configured to detect the reflected laser beam that is reflected from the surface of the living subject; and
a processor configured to process the detected reflected laser beam to determine vibrations of the surface of the living subject.

Clause 40. The apparatus of clause 39, wherein the emitter is a first emitter, the laser beam is a first laser beam, and the apparatus further comprises a second emitter configured to emit a second laser beam directed at the surface of the living subject.

Clause 41. The apparatus of clause 40, wherein the second laser beam has different characteristics than the first laser beam.

Clause 42. The apparatus of clause 40, wherein the first laser beam is directed at a first location on the surface of the living subject and the second laser beam is directed at a second location on the surface of the living subject different from the first location.

Clause 43. The apparatus of clause 40, wherein the reflected laser beam is a first reflected laser beam, and further wherein the second laser beam is configured to interact with the surface of the living subject such that a second reflected laser beam reflects from the surface of the living subject, and further wherein the second reflected laser beam has different characteristics from the second laser beam at least in part due to the interaction with the surface of the living subject.

Clause 44. The apparatus of clause 43, wherein the detector is further configured to detect the second reflected laser beam that is reflected from the surface of the living subject.

Clause 45. The apparatus of clause 44, wherein the processor is further configured to process the detected second reflected laser beam to determine vibrations of the surface of the living subject.

Clause 46. The apparatus of clause 40, wherein the second laser beam is either visible or invisible to the human eye.

Clause 47. The apparatus of clause 39, wherein neither the emitter nor the detector come into contact with the surface of the living subject.

Clause 48. A method for measuring vibrations of a surface of a living subject comprising:
emitting a laser beam directed at the surface of the living subject, wherein the laser beam is configured to interact with the surface of the living subject such that a reflected laser beam reflects from the surface of the living subject, and further wherein the reflected laser beam has different characteristics from the laser beam at least in part due to the interaction with the surface of the living subject;
detecting the reflected laser beam that is reflected from the surface of the living subject; and
processing the detected reflected laser beam to determine vibrations of the surface of the living subject.

Clause 49. The method of clause 48, wherein the processing further outputs an audio signal that approximates a sound of the vibrations of the surface of the living subject that would be detected if a stethoscope was used to detect the vibrations.

Clause 50. The method of clause 48, wherein the laser beam is either visible or invisible to a human eye.

Clause 51. The method of clause 50, wherein the laser beam is invisible to the human eye and is a first laser beam, and the method further comprises emitting a second laser beam that is visible to the human eye, wherein the second laser beam is configured to illuminate a point of the surface of the living subject at which the first laser beam is directed.

Clause 52. The method of clause 48, wherein the processing further filters out ambient noise and light interference.

Clause 53. The method of clause 48, further comprising outputting, based on the processing, a visualization indicative of the vibrations to a display of a computing device.

Clause 54. The method of clause 48, wherein the laser beam is modulated with a carrier frequency, and the processing further comprises demodulating the carrier frequency from the reflected laser beam.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations of methods and systems. It is understood that each block of the block diagrams or operational illustrations, and combinations of blocks in the block diagrams or operational illustrations, can be implemented by means of analog or digital hardware and computer program instructions. These computer program instructions can be provided to a processor of a general-purpose computer to alter its function as detailed herein, a special purpose computer, ASIC, or other programmable data processing apparatus (e.g., PLC), such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

For the purposes of this disclosure any computer readable medium (or computer-readable storage medium/media) stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid-state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

What is claimed is:

1. An apparatus comprising:
a light;
a lens positioned over the light;
a switch to turn the light on or off;
a clipping mechanism configured to removably attach the apparatus to a bell portion of a stethoscope; and
at least one capacitive touch sensor configured to adjust a brightness of the light in response to sensing a finger of a user,
wherein:
the switch is accessible to a user while the apparatus is attached to the bell portion with the clipping mechanism,
the apparatus is configured not to block any portion of a diaphragm of the stethoscope while the apparatus is attached to the bell portion with the clipping mechanism,
the apparatus is configured to enter a sleep mode that consumes less power than a normal operating mode upon a determination that the at least one capacitive touch sensor has not sensed a presence of the finger of the user within a predetermined amount of time, and
the at least one capacitive touch sensor is proximate to the lens, such that the at least one capacitive touch sensor is configured to sense a presence of the finger of the user through the lens.

2. The apparatus of claim 1, wherein the clipping mechanism comprises flexible, rubberized plastic configured to deflect when attaching the apparatus to the stethoscope or detaching the apparatus from the stethoscope, and further wherein the flexible, rubberized plastic is configured to dampen noise from passing from the apparatus into the stethoscope.

3. The apparatus of claim 1, wherein the clipping mechanism is configured to fit on at least two different sized bells of at least two different stethoscopes.

4. The apparatus of claim 1, wherein the clipping mechanism comprises at least two arms configured to wrap around an outer perimeter of the bell portion.

5. The apparatus of claim 4, wherein at least one arm of the at least two arms is operably connected to a spring, such that the at least one arm is movable when attaching the apparatus to the bell portion and the spring holds the at least one arm in place after the apparatus is attached to the bell portion.

6. The apparatus of claim 1, wherein the light is powered by a battery and the battery is at least one of:
stored directly in the apparatus; or
stored in a different portion of the stethoscope than the apparatus and wherein the apparatus is electrically connected to the different portion through an electrical wire.

7. The apparatus of claim 6, wherein the battery is stored in the different portion of the stethoscope, and the electrical wire is removably connected to the apparatus.

8. The apparatus of claim 6, wherein the battery is stored directly in the apparatus, and the apparatus further comprises a port for removably connecting a device to the apparatus, such that the device is powered by the battery.

9. The apparatus of claim 6, wherein the stethoscope is an electronic stethoscope comprising:
a microphone configured to generate an electrical signal in response to received sound from a living subject;
amplification circuitry operably coupled to the microphone and configured to amplify the electric signal generated by the microphone; and
a speaker operably coupled to the amplification circuitry and configured to output the electric signal after amplification,
wherein the battery powers at least one of the microphone, the amplification circuitry, or the speaker.

10. The apparatus of claim 9, wherein the microphone is embedded into tubing connected between a diaphragm and an ear piece of the electronic stethoscope, wherein the tubing is configured to allow acoustic sound waves to travel from the diaphragm to the ear piece, and wherein the microphone does not impede the acoustic sound waves from traveling within the tubing.

11. The apparatus of claim 6, further comprising a percussive device configured to apply a percussive force to a living subject, the percussive device comprising:
a membrane having a first surface and a second surface, wherein the first surface is opposite the second surface; and
a linear actuator configured to move a plunger linearly in response to application or removal of an electrical signal,
wherein:
the linear actuator is configured to move the plunger such that the plunger impacts the first surface of the membrane,
the membrane is configured to transmit a percussive force from the first surface to the second surface as a result of the plunger impacting the first surface of the membrane, and
the linear actuator is powered by the battery.

12. The apparatus of claim 11, wherein the linear actuator comprises an electromechanical solenoid or a voice coil.

13. The apparatus of claim 11, wherein the percussive device is configured to removably attach to the stethoscope or is incorporated into the stethoscope.

14. The apparatus of claim 11, wherein the electrical signal is a first electrical signal, and further wherein the stethoscope is an electronic stethoscope comprising an acoustic sensor configured to generate a second electrical signal indicative of a response of a living subject to the plunger impacting the membrane and transmitting a percussive force into the living subject.

15. The apparatus of claim 14, wherein the first electrical signal is controlled to cause a desired magnitude and duration of the percussive force.

16. The apparatus of claim 1, wherein the apparatus is generally round in shape, and wherein the apparatus further comprises a plurality of capacitive touch sensors oriented at or near a periphery of the apparatus and configured to adjust the brightness of the light in response to the user moving the finger around the periphery of the apparatus.

17. The apparatus of claim 1, wherein the lens is configured to focus the light in a particular direction.

18. The apparatus of claim 1, wherein the lens is positioned on a side of the apparatus opposite the clipping mechanism.

19. A modular electronic stethoscope apparatus comprising:
an electronic stethoscope module comprising:
a microphone configured to generate an electrical signal in response to received sound from a living object, amplification circuitry operably coupled to the microphone and configured to amplify the electric signal generated by the microphone,
a speaker operably coupled to the amplification circuitry and configured to output the electric signal after amplification, and
a power supply configured to power the amplification circuitry;
a light module comprising:
a light,
a lens positioned over the light,
a switch to turn the light on or off,
a clipping mechanism configured to removably attach the light module to a bell portion of the electronic stethoscope module, and
at least one capacitive touch sensor configured to adjust the brightness of the light in response to sensing the finger of a user,
wherein:
the switch is accessible to a user while the light module is attached to the bell portion with the clipping mechanism,
the light module is configured not to block any portion of a diaphragm of the stethoscope while the light module is attached to the bell portion with the clipping mechanism,
the light module is configured to enter a sleep mode that consumes less power than a normal operating mode upon a determination that the at least one capacitive touch sensor has not sensed a presence of the finger of the user within a predetermined amount of time, and
the at least one capacitive touch sensor is proximate to the lens, such that the at least one capacitive touch sensor is configured to sense a presence of the finger of the user through the lens; and
a percussive module comprising:
a membrane having a first surface and a second surface, wherein the first surface is opposite the second surface, and
a linear actuator configured to move a plunger linearly in response to application or removal of an electrical signal,
wherein:
the linear actuator is configured to move the plunger such that the plunger impacts the first surface of the membrane,
the membrane is configured to transmit a percussive force from the first surface to the second surface as a result of the plunger impacting the first surface of the membrane, and
the percussive module is configured to removably attach to the electronic stethoscope module.

20. An apparatus comprising:
a light;
a lens positioned over the light;
a switch to turn the light on or off;
a clipping mechanism configured to removably attach the apparatus to a tubing portion of a stethoscope; and
at least one capacitive touch sensor configured to adjust a brightness of the light in response to sensing a finger of a user,
wherein:
the switch is accessible to a user while the apparatus is attached to the tubing portion with the clipping mechanism, and
the apparatus is configured not to block any portion of a diaphragm of the stethoscope while the apparatus is attached to the tubing portion with the clipping mechanism,
the apparatus is configured to enter a sleep mode that consumes less power than a normal operating mode upon a determination that the at least one capacitive touch sensor has not sensed a presence of the finger of the user within a predetermined amount of time, and
the at least one capacitive touch sensor is proximate to the lens, such that the at least one capacitive touch sensor is configured to sense a presence of the finger of the user through the lens.

* * * * *